(12) United States Patent
Beaucage et al.

(10) Patent No.: US 6,965,041 B1
(45) Date of Patent: Nov. 15, 2005

(54) N-ACYLPHOSPHORAMIDITES AND THEIR USE IN OLIGONUCLEOTIDE SYNTHESIS

(75) Inventors: Serge L. Beaucage, Silver Spring, MD (US); Andrzej Wilk, Bethesda, MD (US); Andrzej Grajkowski, Bethesda, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/937,292

(22) PCT Filed: Feb. 16, 2000

(86) PCT No.: PCT/US00/04032

§ 371 (c)(1),
(2), (4) Date: Jan. 25, 2002

(87) PCT Pub. No.: WO00/56749

PCT Pub. Date: Sep. 28, 2000

Related U.S. Application Data

(60) Provisional application No. 60/125,867, filed on Mar. 24, 1999.

(51) Int. Cl.[7] ........................ C07D 407/12; C07H 21/00
(52) U.S. Cl. .................... 549/472; 536/25.3; 536/26.11
(58) Field of Search ........................ 549/472; 536/26.11, 536/25.3

(56) References Cited

U.S. PATENT DOCUMENTS

| | | | |
|---|---|---|---|
| 3,534,017 A | 10/1970 | Fujimoto et al. |
| 4,415,732 A | 11/1983 | Caruthers et al. |
| 4,417,046 A | 11/1983 | Hsiung et al. |
| 4,458,066 A | 7/1984 | Caruthers et al. |
| 4,663,446 A | 5/1987 | Wright |
| 4,668,777 A | 5/1987 | Caruthers et al. |
| 4,725,677 A | 2/1988 | Köster et al. |
| 4,739,044 A | 4/1988 | Stabinsky |
| 4,757,141 A | 7/1988 | Fung et al. |
| 4,808,708 A | 2/1989 | Yoshida et al. |
| 4,816,569 A | 3/1989 | Miyoshi |
| 4,816,570 A | 3/1989 | Farquhar |
| 4,845,205 A | 7/1989 | Huynh Dinh et al. |
| 4,849,513 A | 7/1989 | Smith et al. |
| 4,950,745 A | 8/1990 | Ishido et al. |
| 4,973,679 A | 11/1990 | Caruthers et al. |
| 4,980,460 A | 12/1990 | Molko et al. |
| 5,026,838 A | 6/1991 | Nojiri et al. |
| 5,039,796 A | 8/1991 | Engels et al. |
| 5,071,974 A | 12/1991 | Groody |
| 5,091,519 A | 2/1992 | Cruickshank |
| 5,134,228 A | 7/1992 | Takaku |
| RE34,069 E | 9/1992 | Köster et al. |
| 5,166,330 A | 11/1992 | Engels et al. |
| 5,212,304 A | 5/1993 | Fung et al. |
| 5,214,135 A | 5/1993 | Srivastava et al. |
| 5,252,760 A | 10/1993 | Urdea et al. |
| 5,258,538 A | 11/1993 | Fung et al. |
| 5,324,831 A | 6/1994 | Marquez et al. |
| 5,332,845 A | 7/1994 | Ureda et al. |
| 5,348,868 A | 9/1994 | Reddy et al. |
| 5,428,148 A | 6/1995 | Reddy et al. |
| 5,430,138 A | 7/1995 | Urdea et al. |
| 5,449,602 A | 9/1995 | Royer et al. |
| 5,506,351 A | 4/1996 | McGee |
| 5,510,476 A | 4/1996 | Ravikumar et al. |
| 5,518,651 A | 5/1996 | Reddy et al. |
| 5,519,126 A | 5/1996 | Hecht |
| 5,525,719 A | 6/1996 | Srivastava et al. |
| 5,556,961 A | 9/1996 | Foote et al. |
| 5,571,902 A | 11/1996 | Ravikumar et al. |
| 5,574,146 A | 11/1996 | Reddy et al. |
| 5,614,622 A | 3/1997 | Iyer et al. |
| 5,616,700 A | 4/1997 | Reddy et al. |
| 5,623,068 A | 4/1997 | Reddy et al. |
| 5,639,867 A | 6/1997 | Brill |
| 5,645,985 A | 7/1997 | Froehler et al. |
| 5,646,265 A | 7/1997 | McGee |
| 5,652,358 A | 7/1997 | Pfleiderer et al. |
| 5,670,489 A | 9/1997 | Baxter et al. |

(Continued)

FOREIGN PATENT DOCUMENTS

| | | |
|---|---|---|
| EP | 0006220 A | 1/1980 |
| EP | 0090789 A | 10/1983 |
| EP | 0196101 A | 10/1986 |

OTHER PUBLICATIONS

Barone et al., *Nuc. Acids. Res.*, 12 (10) 4051–4061 (1984).
Beaucage et al., *Annals of the N.Y. Acad of Sciences*, 616, 483–485 (1990).

(Continued)

*Primary Examiner*—Taofiq Solola
(74) *Attorney, Agent, or Firm*—Leydig, Voit & Mayer, Ltd.

(57) ABSTRACT

The present invention provides a compound of formula (I), (II), or (III), wherein $R^1$, $R^2$, $R^{2'}$, $R^3$, and $R^{3'}$ are the same or different and each is H an alkyl, an alkenyl, an alkynyl, a cycloalkyl, an aryl, or an aralkyl. Alternatively, either of $R^2$ or $R^{2'}$ combined with either of $R^3$ or $R^{3'}$ comprises a ring. $R^4$ is a protecting group or a solid support $R^5$ is H or an alkyl. $R^6$ is a protecting group, an amidoalkyl, an alkyl, an alkyl ketone, an alkenyl, an alkynyl, a cycloalkyl, an aryl, or an aralkyl. $R^{15}$ is H or a protecting group. Q and $Q^1$ are the same or different and each is a nucleoside, an oligonucleotide comprising a nucleoside, or an oligomer comprising a nucleoside, which is of formula (a) or (b), wherein B is a labeling group, an alkyl, an alkenyl, an alkynyl, a cyclic group optionally containing one or more heteroatoms, or an amino; and, E is H, a halogen, a hydroxy, an alkoxy, an ester, an amino or a protecting group. X and $X^1$ are independently O, S, or Se, and n is an integer from 1 to about 300. Each Q in each monomeric unit defined by n can be the same or different. The present invention further provides a method of preparing a polymer using the N-acylphosphoramidite of formula (I) or (II).

20 Claims, 13 Drawing Sheets

U.S. PATENT DOCUMENTS

| | | | |
|---|---|---|---|
| 5,681,940 | A | 10/1997 | Wang et al. |
| 5,700,919 | A | 12/1997 | Seliger et al. |
| 5,703,218 | A | 12/1997 | Urdea et al. |
| 5,703,223 | A | 12/1997 | Wickstrom et al. |
| 5,705,621 | A | 1/1998 | Ravikumar |
| 5,712,378 | A | 1/1998 | Wang |
| 5,714,597 | A | 2/1998 | Ravikumar et al. |
| 5,731,429 | A | 3/1998 | Reddy et al. |
| 5,763,599 | A | 6/1998 | Pfleiderer et al. |
| 5,866,700 | A | 2/1999 | Pfleiderer et al. |
| 5,889,165 | A | 3/1999 | Fodor et al. |
| 5,908,926 | A | 6/1999 | Pirrung et al. |
| 5,959,099 | A | 9/1999 | Cheruvallath et al. |
| 6,001,982 | A | 12/1999 | Ravikumar et al. |
| 6,022,963 | A | 2/2000 | McGall et al. |
| 6,043,060 | A | 3/2000 | Imanishi |
| 2001/0044529 | A1 | 11/2001 | Beaucage et al. |

OTHER PUBLICATIONS

Beaucage et al., *Tetrahedron*, 48 (12) 2223–2311 (1992).
Beaucage, *Methods in Mol. Biol., 20: Protocols for Oligonucleotides and Analogs, Synthesis and Properties*, 33–61, edited by Sudhir Agrawal, Totowa, N.J., Humana Press (1993).
Beaucage et al., *Current Protocols in Nucleic Acid Chemistry vol. 1*, 3.3.1–3.3.19, John Wiley & Sons, (2000).
Bigg et al., *Synthesis: J. Synthetic Org. Chem.*, 277–278 (1992).
Boal et al., *Nuc. Acids. Res.*, 24 (15), 3115–3117 (1996).
Finger et al., *J. Am. Chem. Soc.*, 2674–2675 (1959).
Gray et al., *J. Am. Chem. Soc.*, 81, 4351–4355 (1959).
Iyer et al., *J. Org. Chem.*, 55, 4693–4699 (1990).
Iyer, *Current Protocols in Nucleic Acid Chemistry, vol. 1*, 2.1.1–2.1.17, John Wiley & Sons, (2000).
Lefebvre, et al., *J. Med. Chem.*, 38, 3941–3950 (1995).
Martin, *Helv. Chim. Acta*, 78, 486–504 (1995).
McBride et al., *J. Am. Chem. Soc.*, 108, 2040–2048 (1986).
Mizrakh et al., *Chem. Abs.*, 83, 454, 193184h, (1975).
Mizrakh et al., *Zh. Obs. Khim.*, 45 (3), 549–552 (Mar. 1975).
Murphy et al., *Tetrahedron*, 47 (24), 4077–4088 (1991).
Prakash et al., *Org. Lett.*, 2 (25), 3995–3998 (2000).
Probst et al., *Makromol. Chem.*, 177, 2681–2695 (1976).
Regan et al., *Org. Preparations and Proc. Intl.*: 24 (4), 488–492(1992).
Saegusa et al., *Makromol. Chem.*, 177, 2271–2283 (1976).
Shibanuma et al., *Chem. Pharm. Bull.*, 28 (9), 2609–2613 (1980).
Smith et al., *Nucelosides & Nucleotides*, 15 (10), 1581–1594 (1996).
Somei et al., *Chem. Pharm. Bull.*, 28 (8), 2515–2518 (1980).
Stec et al., *Nuc. Acids Res.*, 19 (21), 5883–5888 (1991).
Tsuruoka et al., *Tetrahedron Letters*, 40, 8411–8414 (1999).
Waldner et al., *Bioorg. & Medicinal Chem. Lett.*, 6 (19), 2363–2366 (1996).
Weiner et al., *J. Org. Chem.*, 868–872 (1949).
Wilk et al., *J. Org. Chem.*, 62, 6712–6713 (1997).
Wilk et al., *J. Org. Chem.*, 64, 7515–7522 (1999).
Wilk et al., *J. Am. Chem. Soc.*, 122, 2149–2156 (2000).
Wilk et al., *Tetrahedron Letters*, 42, 5635–5639 (2001).
Wilk et al., *J. Org. Chem.*, 67, 6430–6438 (2002).
Wincott, *Current Protocols in Nucleic Acid Chemistry, vol. 1*, 3.5.1–3.5.12, John Wiley & Sons, (2000).
Beaucage et al., *Tetrahedron*, 49(28), 6123–6194 (1993).
Brown et al., *J. Chem. Soc., Chem. Commun. (Royal Society of Chemistry)*, 891–893 (1989).
Cao et al., *Tetrahedron Lett.*, 24(10), 1019–1020 (1983).
Gardrat et al., *J. Heterocycl. Chem*, 27, 811–812 (Mar.–Apr. 1990).
Grajkowski et al., *Org. Lett.*, 3(9), 1287–1290 (Dec. 2001).
Guzaev et al., *Tetrahedron Lett.*, 41, 5623–5626 (2000).
Iyer et al., *J. Org. Chem.*, 60, 5388–5389 (1995).
Iyer et al., *Tetrahedron: Assymetry*, 6(5), 1051–1054 (1995).
Kawanobe et al., *Chem. Lett. (Chemical Society of Japan)*, 825–828 (1982).
Mizrakh et al., *Zh. Obschei Khimii*, 45 (7), 1469–1473 (Jul. 1975).
Mizrakh et al., *Zh. Obschei Khimii*, 45 (10), 2343–2344 (Oct. 1975).
Pudovik et al., "N–Acylated Oxazaphospholanes and Phosphorinanes," Chem. Abstracts, 79 (11): 66261y (1973).
Pudovik et al., "Synthesis of N–Acylated 1, 3, 2–Oxaazaphospholanes," Chem. Abstracts, 81 (11): 63723f (1974).
Scremin et al., *J. Org. Chem.*, 59 (8), 1963–1966 (Apr. 22, 1994).
Smith et al., *Nucleosides & Nucleotides*, 15 (10), 1581–1594 (1996).
Stec et al., *Nucleic Acids Res.*, 21, 5883–5888 (Nov. 11, 1991).
Waldner et al., *Bioorg Med. Chem. Letters*, 6 (19), 2363–2366 (1996).
Wang et al., *Tetrahedron Lett.*, 38 (22), 3797–3800 (1997).
Yang et al., *Chem. Abstracts, 111*: 97382x (1989).
Zhang et al., *Chem. Abstracts, 126* (2): 18939t (1997).

B = any protected nucleobase
S = solid support
DMTr = 4,4'-dimethoxytrityl
TMG = N,N,N',N'-tetramethylguanidine d($C_{PS}C_{PS}C$)
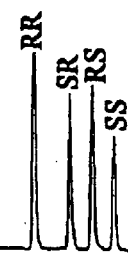
FIG.10A
FIG.10B
FIG.10C
FIG.10D
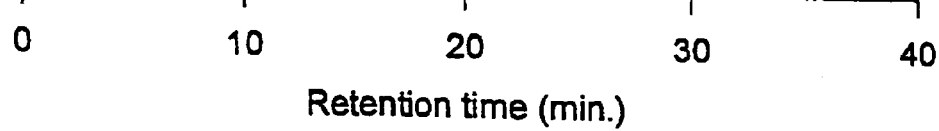
FIG.10E
Retention time (min.)

$d(C_{PS}C_{PS}C_{PS}C)$

Retention time (min.)

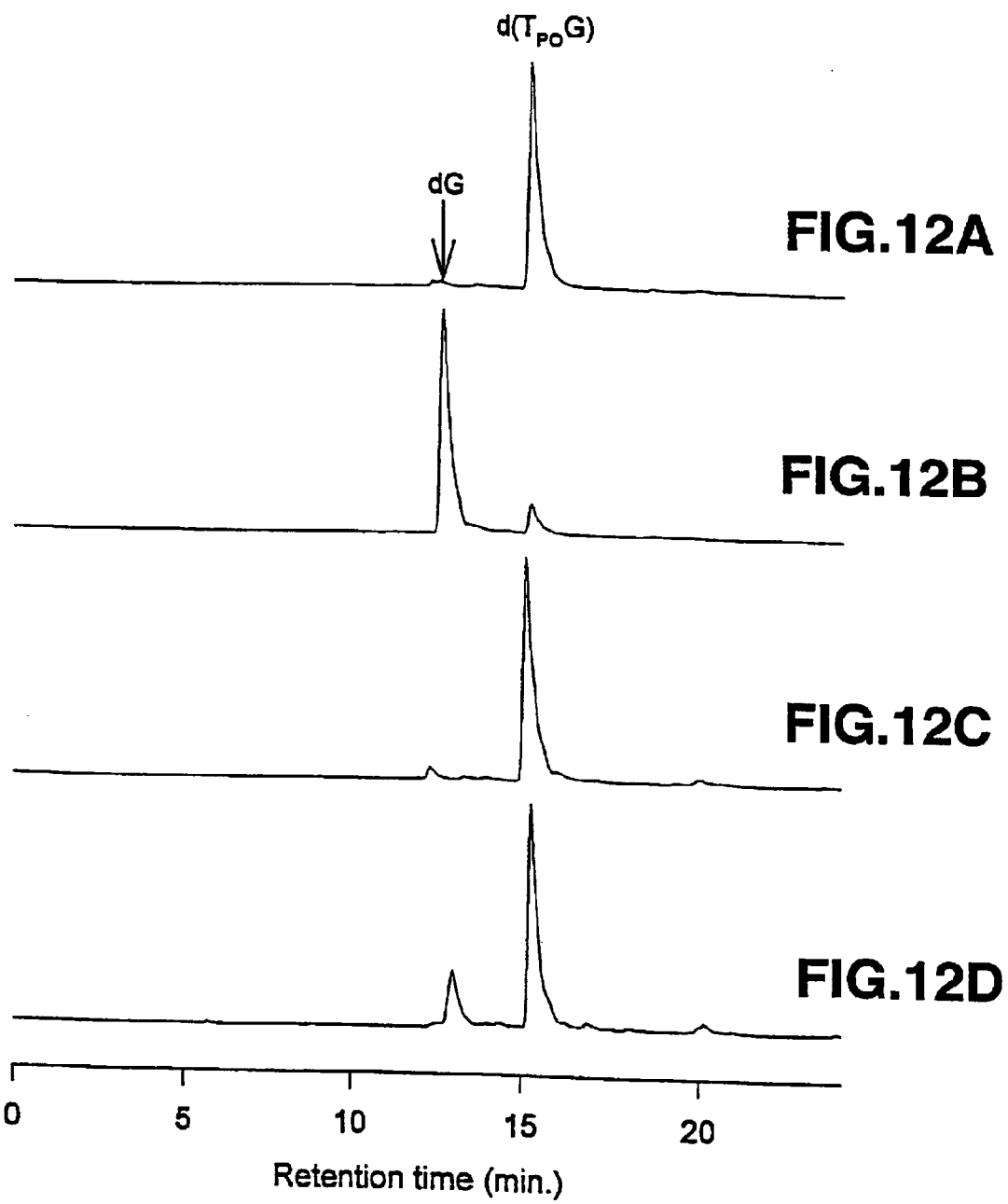

N-ACYLPHOSPHORAMIDITES AND THEIR USE IN OLIGONUCLEOTIDE SYNTHESIS

This appl. is a 371 of PCT/US00/04032 filed Feb. 16, 2002 which claims benefit of 60/125,867 filed Mar. 24, 1999.

TECHNICAL FIELD OF THE INVENTION

The present invention relates to the synthesis of oligonucleotides, and intermediates useful in the synthesis thereof.

BACKGROUND OF THE INVENTION

Since the development of efficient and reliable methods for automated synthesis of oligonucleotides, and early observations about the potential therapeutic application of oligonucleotides, there is a high demand for new oligonucleotide analogues. This demand is due to the fact that natural oligonucleotides undergo very rapid nucleolytic degradation to monomeric nucleosides and nucleotides in biological fluids in vitro and/or in vivo.

The therapeutic application of oligonucleotides is based on the selective formation of hybrids between antisense oligonucleotides and complementary nucleic acids, such as messenger RNAs (mRNAs). Such hybrids inhibit gene expression by blocking protein translation. Successful inhibition of gene expression, however, requires the antisense oligonucleotide to be nuclease resistant so that it can be transported through biological membranes and can hybridize selectively to a target complementary nucleic acid, thereby actively blocking protein translation. Among the diverse oligonucleotide analogues that have been tested for antisense activity, those bearing phosphorothioate internucleotide linkages are the most nuclease resistant and, therefore, are the most widely used.

Oligonucleotides bearing phosphorothioate internucleotide linkages are typically prepared by sulfurization of a phosphite precursor which, in effect, substitutes a sulfur atom for one of the non-bridging oxygen atoms normally present in phosphodiesters. This substitution results in a stereogenic center at the phosphorus atom. Unfortunately, the sulfurization of oligonucleotide phosphodiesters prepared by conventional methods results in the formation of complex mixtures of diastereomers, since the precursors are typically diastereomeric with respect to phosphorus. The stereochemistry of the phosphorus center, however, is important in imparting nucleolytic stability in the oligonucleotide. Structural studies suggest that chirality at the phosphorus center alters the thermodynamics of duplex formation and the pharmacokinetic profiles of therapeutic oligonucleotides. Thus, synthetic methods and intermediates that enable one to control the stereochemistry of such thioated oligonucleotides and to prepare particular thioated oligonucleotides in high stereochemical purity are highly desired. Such methods and intermediates would enable one to optimize the nucleolytic stability of phosphorothioate oligonucleotides. It is even more desirable to develop synthetic methods and intermediates that enable one to control the stereochemistry of tricoordinated, as well as thioated, oligonucleotides and to prepare them in high stereochemical purity.

The most commonly used synthetic method for the synthesis of thioated oligonucleotides is the phosphoramidite method with stepwise sulfurization (see, e.g., U.S. Pat. Nos. 4,415,732, 4,668,777, 4,973,679, 4,845,205, and 5,525,719). This method uses tricoordinated phosphorus precursors that normally produce products containing a mixture of different thioated oligonucleotide stereoisomers. The lack of stereoselectivity in the phosphoramidite process is primarily due to the non-stereoselective and non-stereospecific acid-catalyzed nucleophilic substitution reaction, which is typically required to effect substitution. Even when diastereomerically pure P-chiral precursors are used, the coupling reaction proceeds with full epimerization at phosphorus.

Attempts have been made to control the stereochemistry of phosphorus in the synthesis of oligonucleotides. One attempt is a recently developed stereoselective method, which is drawn to the synthesis of thioated oligonucleotides using tricoordinated phosphorus precursors for acid-catalyzed nucleophilic substitution reactions. However, this approach has narrow applicability, in that it is limited to the synthesis of very short oligomers, particularly because each successive nucleoside coupling step occurs without complete stereoselectivity.

Another attempt at controlling phosphorus stereochemistry in oligonucleotide synthesis involves a method for the stereospecific synthesis of thioated oligonucleotides utilizing tetracoordinated phosphorus precursors to accommodate base-catalyzed nucleophilic substitutions. However, this approach also has limited applicability because a different type of tetracoordinated phosphorus precursor must be used to generate a particular type of product, for example, phosphates, phosphorothioates and phosphoroselenoates. In other words, the structure of the desired product is determined by the structure of the tetracoordinated phosphorus precursor at the coupling step. Additionally, separation of the diastereomers is difficult, and these tetracoordinated phosphorus precursors also are hydrolytically unstable.

In view of the foregoing problems, there exists a need for methods and intermediates that will permit the efficient synthesis of unmodified or modified oligonucleotides, particularly P-chiral oligonucleotides, with high stereospecificity. The present invention provides such methods and associated intermediates. These and other advantages of the present invention, as well as additional inventive features, will be apparent from the description of the invention provided herein.

BRIEF SUMMARY OF THE INVENTION

The present invention provides a compound of the formula:

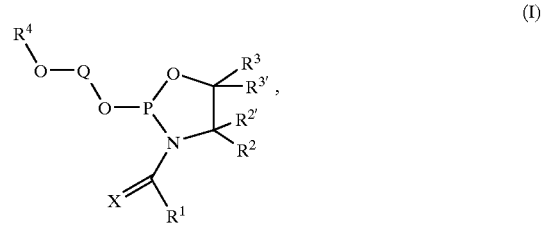

(I)

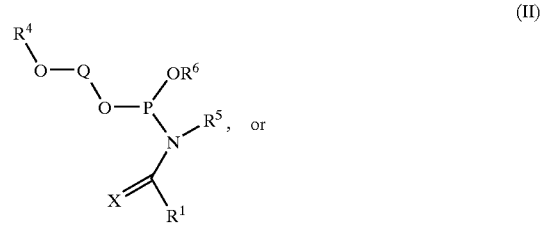

(II)

or

-continued

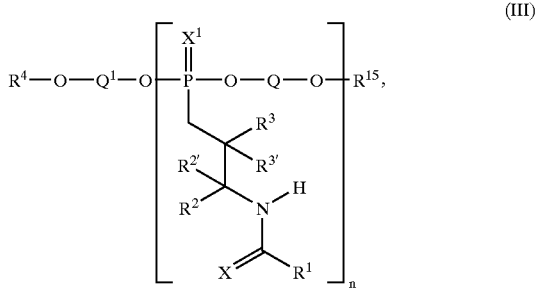

(III)

wherein $R^1$ is an alkyl, an alkenyl, an alkynyl, a cycloalkyl, an aryl, or an aralkyl, wherein $R^1$ is unsubstituted or substituted. $R^2$ and $R^{2'}$ are the same or different and each is H, an alkyl, an alkenyl, an alkynyl, a cycloalkyl, an aryl, or an aralkyl, wherein $R^2$ and/or $R^{2'}$ is unsubstituted or substituted. $R^3$ and $R^{3'}$ are the same or different and each is H, an alkyl, an alkenyl, an alkynyl, a cycloalkyl, an aryl, or an aralkyl, wherein $R^3$ and/or $R^{3'}$ is unsubstituted or substituted. Alternatively, either of $R^2$ or $R^{2'}$, in combination with either of $R^3$ or $R^{3'}$, together with the carbon atoms to which they are bonded, form a cyclic substituent, which can be unsubstituted or substituted. $R^4$ is a protecting group or a solid support. $R^5$ is H or an alkyl, which is unsubstituted or substituted. $R^6$ is a protecting group, an amidoalkyl in which the nitrogen atom thereof is 2, 4, or 5 carbon atoms removed from the oxygen of $OR^6$, an alkyl, an alkyl ketone, an alkenyl, an alkynyl, a cycloalkyl, an aryl, or an aralkyl, wherein $R^6$ is unsubstituted or substituted. $R^{15}$ is H or a protecting group. Q and $Q^1$ are the same or different and each is a nucleoside, a oligonucleotide comprising a nucleoside, or an oligomer comprising a nucleoside, wherein the nucleoside is of the formula:

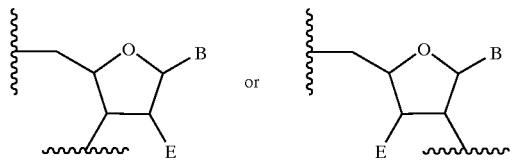

wherein:
B is a labeling group, an alkyl, an alkenyl, an alkynyl, a cycloalkyl, an aryl, a heteroaryl, a heterocycloalkyl, an aralkyl, an amino, an alkylamino, a dialkylamino, a purine, a pyrimidine, adenine, guanine, cytosine, uracil, or thymine, wherein B is unsubstituted or substituted, and E is H, a halogen, $OR^{13}$, $NHR^{13}$, $NR^{13}R^{14}$, wherein $R^{13}$ and $R^{14}$ are the same or different and each is H, a protecting group, an alkyl, or an acyl. X and $X^1$ are the same or different and each is O, S, or Se, and n is an integer from 1 to about 300. Q can be the same or different in each of the units defined by n of formula (III), when n is greater than 1.

The present invention further provides a method of preparing a polymer, including the steps of:
(a) reacting a nucleophile that can displace the N-acyl group of an N-acylphosphoramidite with an N-acylphosphoramidite of formula (I) or (II), wherein $R^4$ is a protecting group, preferably in the presence of a base, to produce an adduct of the N-acylphosphoramidite and the nucleophile, which adduct comprises a tricoordinated phosphorus atom;
(b) reacting the adduct with a reagent selected from the group consisting of oxidizing agents, sulfurizing agents, and selenizing agents, to produce a product, wherein the tricoordinated phosphorus atom is converted into a tetracoordinated phosphorus atom; and
(c) removing $R^4$ from the product to produce another adduct comprising a nucleophilic substituent. The method can further comprise repeating steps (a) through (c), one or more times as necessary, until a polymer of specified length is obtained.

BRIEF DESCRIPTION OF THE DRAWINGS

FIG. 10A illustrates the HPLC chromatogram for a mixture of the four possible P-diastereomeric oligonucleotide phosphorothioate trimers $d(C_{PS}C_{PS}C)$ prepared using standard phosphoramidite chemistry.

FIG. 10B illustrates the HPLC chromatogram for the pure $S_p,S_p$ diastereomer of $d(C_{PS}C_{PS}C)$ prepared in accordance with the present invention.

FIG. 10C illustrates the HPLC chromatogram obtained by co-injecting the pure $S_p,S_p$ diastereomer of $d(C_{PS}C_{PS}C)$ with the mixture containing all four possible P-diastereomers.

FIG. 10D illustrates the HPLC chromatogram for the pure $R_p,R_p$ diastereomer of $d(C_{PS}C_{PS}C)$, prepared in accordance with the present invention.

FIG. 10E illustrates the HPLC chromatogram obtained by co-injecting the pure $R_p,R_p$ diastereomer of $d(C_{PS}C_{PS}C)$ with the mixture containing all four possible P-diastereomers.

FIG. 12A illustrates the HPLC chromatogram for the dimeric phosphodiester d($T_{PO}G$) prepared under standard phosphoramidite coupling conditions in the absence of moisture.

FIG. 12B illustrates the HPLC chromatogram for the product obtained in the preparation of dimeric phosphodiester d($T_{PO}G$) under standard phosphoramidite coupling conditions in the presence of moisture (0.1% water).

FIG. 12C illustrates the HPLC chromatogram for the dimeric phosphodiester d($T_{PO}G$) prepared by an N-acylphosphoramidite coupling reagent of the present invention in the absence of moisture.

FIG. 12D illustrates the HPLC chromatogram for the product obtained in the preparation of dimeric phosphodiester d($T_{PO}G$) by an N-acylphosphoramidite coupling reagent of the present invention in the presence of moisture (0.1% water).

DESCRIPTION OF THE PREFERRED EMBODIMENTS

Figure 1:
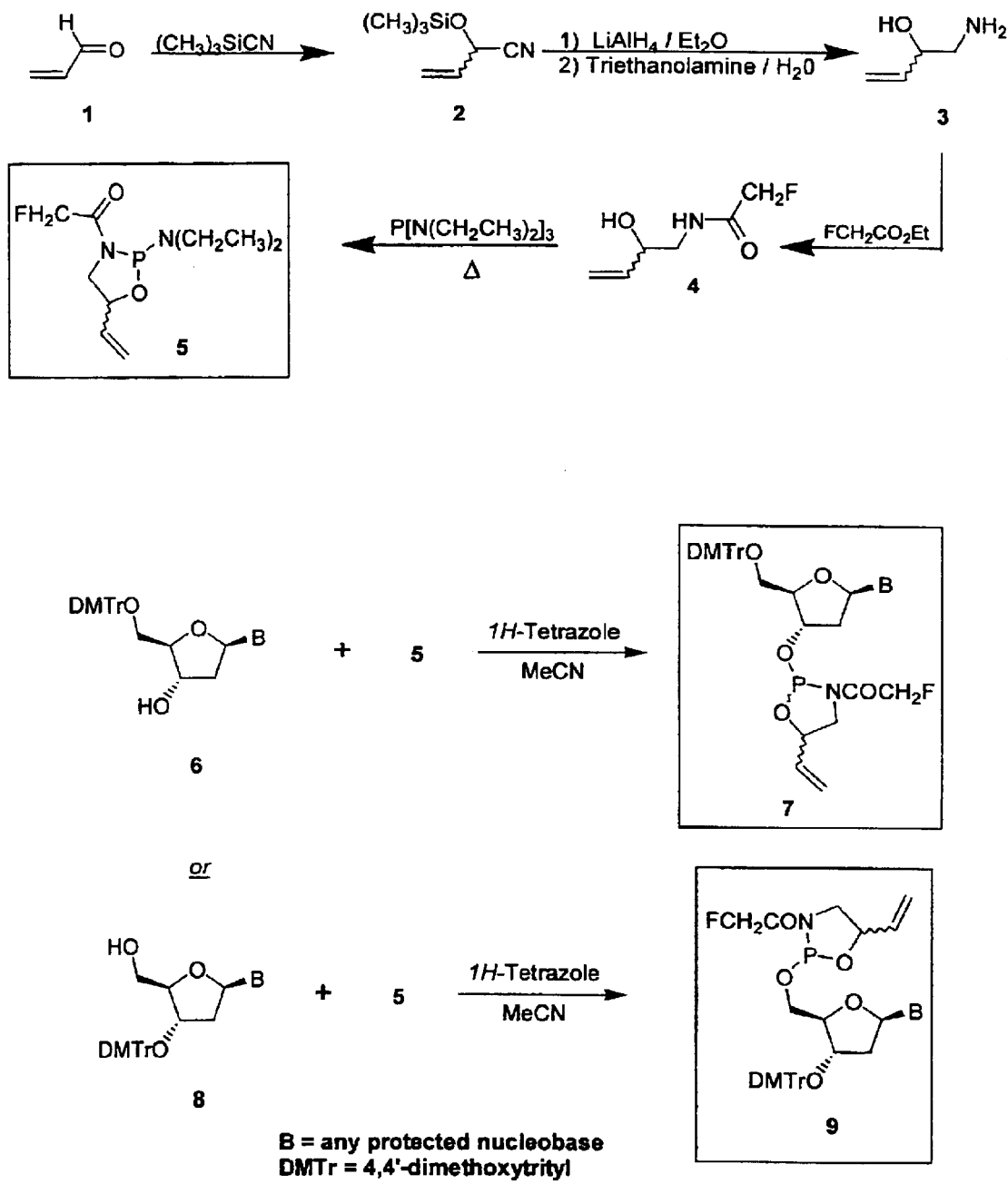
FIG. 1 illustrates the synthesis of an N-acylphosphoramidite.

The present invention is predicated, at least in part, on the surprising and unexpected discovery that the utilization of N-acylphosphoramidites as a coupling vehicle, for example, with respect to the coupling of nucleoside-containing fragments, occurs without any epimerization at phosphorus. Moreover, post-coupling reactions and transformations (i.e., the synthetic steps that are carried out after step (b) of the method as set forth below), for example, oxidation, sulfurization, and deprotection, occur without epimerization at the phosphorus atom.

The present inventive method of synthesizing polymers has tremendous synthetic advantages that are unprecedented in the art, particularly with respect to the synthesis of oligonucleotides, in that it enables the facile production of P-chiral oligomeric or polymeric products, with complete control of stereochemistry with respect to the phosphorus atom. Moreover, stereochemistry can be controlled for tri-coordinated and tetracoordinated phosphorus atoms.

Although applicants do not wish to be bound by any one particular theory, it is believed that the N-acyl functionality of the N-acylphosphoramidite ring (which functions as a leaving group in coupling step (b) of the method as set forth below) is not labile under the coupling conditions utilized for the displacement thereof; rather, displacement occurs via a purely bimolecular nucleophilic mechanism. As such, there is no "scrambling" or epimerization of the phosphorus atom in the coupling step.

By contrast, the standard phosphoramidite approach presently utilized in the art involves displacement of an amino functionality on phosphorus, and requires acidic conditions for the displacement thereof. The phosphorus-nitrogen bond in a standard phosphoramidite is labile under acidic conditions (even when a mild acid such as tetrazole is used), invariably resulting in epimerization of the phosphorus atom in the resulting coupled adduct. Although attempts have been made to control the extent of epimerization in coupling reactions using phosphoramidites, there is inevitably some epimerization, which promotes the formation of diastereomers. Even if the formation of undesired diastereomers occurs in minute quantities, the overall yield of the target product decreases exponentially.

The compounds and methods of the present invention, therefore, provide for the stereospecific substitution of tri-coordinated phosphorus compounds under basic conditions. In this regard, the monomeric compounds of the present invention (preferably of formulae (I) and (II)), and the oligomeric compounds of the present invention (preferably of formula (III)), are particularly useful in the synthesis of polymers, particularly oligonucleotide polymers.

Generally, the compounds of the present invention are hydroxyl-protected monomer-O-(O-protected)-(N-acyl) phosphoramidites, or hydroxyl protected oligomer/polymer-O-(O-protected)-(N-acyl)phosphoramidites, exemplified by formulae (I)–(III).

In a preferred embodiment, the compound is a hydroxyl-protected monomer-O-(N-acyl)-1,3,2-substituted oxazaphospholane (formula (I)), which can be isolated as the Rp or Sp chiral form, to be used in the synthesis of polymers containing stereogenic phosphorus centers of predetermined configuration in a site-specific manner.

In view of the above, the present invention provides a compound of the formula:

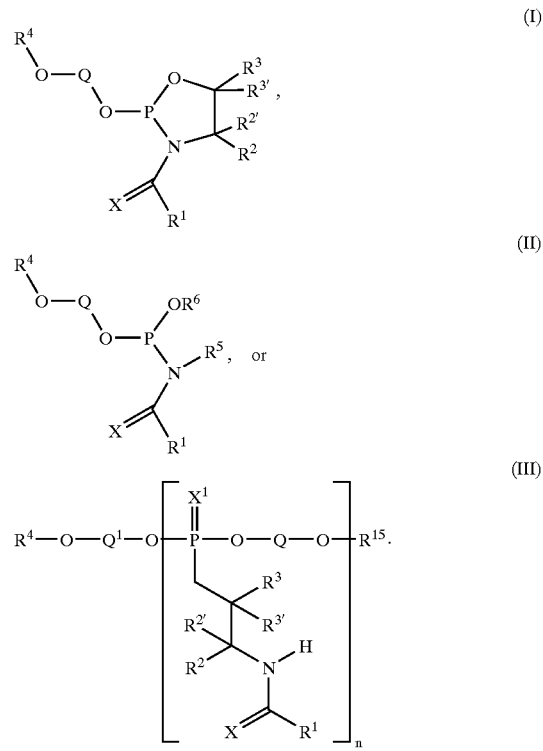

With respect to the above formulae, any suitable acyl moiety can be used. Suitable acyl moieties include $R^1(C=X)N-$ groups which render the phosphorus-(N-acyl) bond sufficiently reactive to allow displacement of the N-acyl group by a nucleophile, preferably under basic conditions. Preferably, $R^1$ is an alkyl (e.g., a $C_1-C_6$ alkyl), an alkenyl (e.g., a $C_2-C_6$ alkenyl), alkynyl (e.g., a $C_2-C_6$ alkynyl), a cycloalkyl (e.g., a $C_3-C_7$ cycloalkyl), an aryl (e.g., phenyl or naphthyl), or an aralkyl (e.g., benzyl, phenethyl, phenylpropyl, or the like), wherein $R^1$ is unsubstituted or is substituted with one or more substituents, which are the same or different, selected from the group consisting of $R^7$, $OR^7$, $SR^7$, $NR^8OR^7$, $NR^8CSR^7$, $NR^8CO_2R^7$, $NR^8C(O)SR^7$, $NR^8CS_2R^7$, $O_2CR^7$, $S_2CR^7$, $SCOR^7$, $OCSR^7$, $SO_2R^7$, $OSO_2R^7$, $NR^8SO_2R^7$ $CN$, $NO_2$, $N_3$, and a halogen, wherein $R^7$ is an alkyl, an aryl, or an aralkyl, wherein $R^7$ is unsubstituted or is substituted with one or more halogen atoms, which are the same or different, and $R^8$ is H or an alkyl. In one embodiment, $R^1$ is an alkyl, which is preferably a $C_1$–$C_6$ alkyl, that is unsubstituted or is substituted with one or more substituents, which are the same or different, selected from the group consisting of fluorine, $OR^7$ and $SR^7$, wherein $R^7$ is an alkyl or an aryl. When $R^1$ is a $C_1$–$C_6$ alkyl, it is more preferably a $C_1$–$C_3$ alkyl which is unsubstituted or substituted with one or more fluorine atoms, for example, a methyl, optionally substituted with one or more fluorine atoms, most preferably fluoromethyl. When $R^1$ is a $C_1$–$C_6$ alkyl substituted with $OR^7$ or $SR^7$, $R^1$ is most preferably a methoxymethyl, a methylthiomethyl or a phenoxy.

While $R^2$ and $R^{2'}$ can be any suitable substituent, preferably $R^2$ and $R^{2'}$ are the same or different and each is H, an alkyl, an alkenyl, an alkynyl, a cycloalkyl, an aryl or an aralkyl. When $R^2$ or $R^{2'}$ is an alkyl, it is preferably a $C_1$–$C_6$ alkyl. When $R^2$ or $R^{2'}$ is an alkenyl, it is preferably a $C_2$–$C_6$ alkenyl. When $R^2$ or $R^{2'}$ is an alkynyl, it is preferably a $C_2$–$C_6$ alkynyl. When $R^2$ or $R^{2'}$ is a cycloalkyl, it is preferably a $C_3$–$C_7$ cycloalkyl. $R^2$ and/or $R^{2'}$ can be unsubstituted or substituted with one or more substituents selected from the group consisting of $OR^7$, CN, $NO_2$, $N_3$, and a halogen. In a particularly preferred embodiment, $R^2$ and $R^{2'}$ are hydrogen.

While $R^3$ and $R^{3'}$ can be any suitable substituent, preferably $R^3$ and $R^{3'}$ are the same or different and each is H, an alkyl, an alkenyl, an alkynyl, a cycloalkyl, an aryl or an aralkyl. When $R^3$ or $R^{3'}$ is an alkyl, it is preferably a $C_1$–$C_6$ alkyl. When $R^3$ or $R^{3'}$ is an alkenyl, it is preferably a $C_2$–$C_6$ alkenyl. When $R^3$ or $R^{3'}$ is an alkynyl, it is preferably a $C_2$–$C_6$ alkynyl. When $R^3$ or $R^{3'}$ is a cycloalkyl, it is preferably a $C_3$–$C_7$ cycloalkyl. $R^3$ and/or $R^{3'}$ can be unsubstituted or substituted with one or more substituents selected from the group consisting of a trialkylsilyl, an aryldialkylsilyl, an alkyldiarylsilyl, CN, $NO_2$, $N_3$, a halogen, $OR^7$, $P(O)(OR^7)$ $(OR^8)$, $COR^9$, $CSR^9$, $CO_2R^9$, $COSR^9$, $CSOR^9$, $CONR^8R^9$, $CSNR^8R^9$, $SO_2R^9$, and $SO_2NR^8R^9$, wherein $R^7$ is as defined herein. While $R^9$ can be any suitable substituent, $R^9$ preferably is H, an alkyl, an alkenyl, an alkynyl, a cycloalkyl, an aryl or an aralkyl. When $R^9$ is an alkyl, it is preferably a $C_1$–$C_6$ alkyl. When $R^9$ is an alkenyl, it is preferably a $C_2$–$C_6$ alkenyl. When $R^9$ is an alkynyl, it is preferably a $C_2$–$C_6$ alkynyl. When $R^9$ is a cycloalkyl, it is preferably a $C_3$–$C_7$ cycloalkyl. $R^9$ can be unsubstituted or it can be substituted with one or more substituents selected from the group consisting of CN, $NO_2$, $N_3$, and a halogen.

There are certain preferred combinations of $R^2$–$R^{3'}$. In one preferred embodiment, $R^3$ is a phenyl, $R^2$, $R^{2'}$ and $R^{3'}$ all are H, and $R^1$ is selected from the group consisting of methyl, fluoromethyl, methoxymethyl and phenoxymethyl. In another preferred embodiment, $R^3$ is a vinyl, $R^2$ is H, and $R^3$ is selected from the group consisting of methyl, fluoromethyl, methoxymethyl and phenoxymethyl. In yet another preferred embodiment, $R^3$ and $R^2$ are both H, and $R^1$ is a methyl.

Alternatively, $R^2$ and $R^3$, $R^2$ and $R^{3'}$, $R^{2'}$ and $R^3$, and $R^{2'}$ and $R^{3'}$, together with the carbon atoms to which they are bonded, comprise a cyclic substituent. In other words, a combination of either of $R^2$ and $R^{2'}$ with either of $R^3$ and $R^{3'}$ can comprise a cyclic substituent. Preferably, $R^2$ or $R^{2'}$ and $R^3$ or $R^{3'}$, together with the carbon atoms to which they are bonded, comprise a cyclic substituent of the formula:

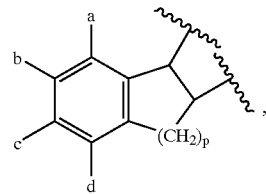

wherein p is an integer from 0–6 and a–d are the same or different and each is selected from the group consisting of H, an alkyl, a nitro, an amino, a hydroxy, a thio, a cyano and a halogen. In a preferred embodiment, p is 1 and all of a–d are H. In a particularly preferred embodiment, p is 1, all of a–d are H, and $R^1$ is fluoromethyl.

$R^4$ is a protecting group or a solid support.

$R^5$ is H or an alkyl, preferably a $C_1$–$C_3$ alkyl, which can be unsubstituted or substituted with one or more substituents, which are the same or different, selected from the group consisting of $OR^7$, CN, $NO_2$, $N_3$, and a halogen, wherein $R^7$ is as defined herein.

While $R^6$ can be any suitable substituent, $R^6$ preferably is a protecting group, an alkyl, an amidoalkyl, an alkenyl, an alkynyl, a cycloalkyl, an aryl, an alkyl ketone, or an aralkyl. When $R^6$ is an alkyl, it is preferably a $C_1$–$C_6$ alkyl. When $R^6$ is an amidoalkyl, it is preferably an amidoalkyl, more preferably a $C_1$–$C_6$ amidoalkyl, in which the nitrogen atom thereof is 2, 4, or 5 atoms removed from the oxygen atom of $OR^6$, and is most preferably an amidoalkyl whose amide is easily hydrolyzed or cleaved and liberates an amine which is separated from the oxygen of $OR^6$ by 2, 4, or 5 carbon atoms. When $R^6$ is an alkenyl, it is preferably a $C_2$–$C_6$ alkenyl. When $R^6$ is an alkynyl, it is preferably a $C_2$–$C_6$ alkynyl. When $R^6$ is a cycloalkyl, it is preferably a $C_3$–$C_7$ cycloalkyl. $R^6$ can be unsubstituted or substituted with one or more substituents, which are the same or different, selected from the group consisting of CN, $NO_2$, $N_3$, and a halogen.

$R^{15}$ is H or a protecting group.

Q and $Q^1$ are the same or different and each is a nucleoside, an oligonucleotide comprising a nucleoside, or an oligomer comprising a nucleoside (e.g., an oligonucleotide or the like). Q and/or $Q^1$ can be a natural nucleoside or a modified/unnatural nucleoside. Q and/or $Q^1$ also can be an oligomer comprising one or more natural or modified/unnatural nucleosides. Modified nucleosides can be obtained, for example, by any suitable synthetic method known in the art for preparing nucleosides, derivatives, or analogs thereof. Modified nucleosides include, but are not limited to, chemically modified nucleosides used as building blocks for "labeled" oligonucleotides, or suitable precursors or analogs used in the preparation of such modified nucleosides. Various chemically modified nucleosides are described, for example, in Smith et al., *Nucleosides & Nucleotides*, 15(10), 1581–1594 (1996) ("Smith et al."). Smith et al. describes the synthesis of nucleosides (and oligomers which include such nucleosides) in which the base ring is replaced by a carboxylic acid to which is appended various "labeling" groups (e.g., biotin, cholesterol, fluorenylmethoxycarbonyl (Fmoc), and trifluoroacetyl) via a modified amide linker. Modified nucleosides also include other chemically modified nucleosides, for example, nucleosides described in Smith et al. in which the base ring is replaced by a hydroxyethyl, a cyano, or a carboxylic acid (including esters and amides thereof). Modified nucleosides further include nucleosides in which the base ring is replaced by a cyclic substituent, for example, an aryl, a cycloalkyl, a heterocycloalkyl, or a heteroaryl (other than a base naturally occurring in nucleosides).

Q and/or $Q^1$ also include oligonucleotides, which can be natural or modified. Modified oligonucleotides include, for example, oligonucleotides containing a modified nucleoside (as described herein), oligonucleotides containing a modified internucleotide linkage, or oligonucleotides having any combination of modified nucleosides and internucleotide linkages (even if a natural nucleoside is present in the oligomer chain). Oligonucleotides whose nucleosides are connected via modified internucleotide linkages can be found, for example, in Waldner et al., *Bioorg. Med. Chem. Letters*, 6, 19, 2363–2366 (1996) ("Waldner et al."), which describes the synthesis of oligonucleotides containing various amide internucleotide linkages.

In a preferred embodiment, Q and $Q^1$ are the same or different and each is a nucleoside substituent (or an oligonucleotide comprising a nucleoside, a nucleoside, or an oligomer comprising a nucleoside) of the formula:

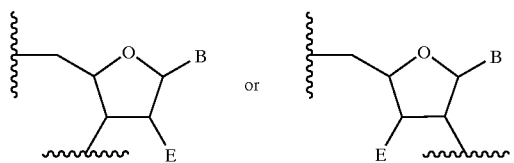

wherein B is a labeling group, an alkyl, an alkenyl, an alkynyl, a cycloalkyl, an aryl, a heteroaryl, a heterocycloalkyl, an aralkyl, an amino, an alkylamino, a dialkylamino, a purine, a pyrimidine, adenine, guanine, cytosine, uracil, or thymine, wherein B is unsubstituted or substituted with one or more substituents, which are the same or different, selected from the group consisting of a protecting group, $R^{11}$, $OR^{11}$, $NHR^{11}$, $NR^{11}R^{12}$, CN, $NO_2$, $N_3$, and a halogen, wherein $R^{11}$ and $R^{12}$ are the same or different and each is H, a protecting group, or an alkyl; and E is H, a halogen, $OR^{13}$, $NHR^{13}$, or $NR^{13}R^{14}$ wherein $R^{13}$ and $R^{14}$ are the same or different and each is H, a protecting group, an alkyl, or an acyl. When B is an alkyl, preferably it is a $C_1$–$C_6$ alkyl. When B is an alkenyl, it is preferably a $C_2$–$C_6$ alkenyl. When B is an alkynyl, preferably it is a $C_2$–$C_6$ alkynyl. When B is a cycloalkyl, preferably it is a $C_3$–$C_7$ cycloalkyl. When $R^{13}$ and/or $R^{14}$ is an alkyl, preferably it is a $C_1$–$C_6$ alkyl.

As indicated above, the Q in the N-acylphosphoramidites of formulae (I) and (II), and the Q and $Q^1$ in the intermediates obtained therefrom (formula (III)), include nucleosides (natural and modified) and oligomers which include one or more of such nucleosides. Any suitable monomer-monomer, monomer-oligomer, oligomer-monomer, or oligomer-oligomer coupling reaction can be accomplished, stereospecifically, using the compounds and methods of the present invention. For example, the N-acylphosphoramidite of formula (I) or (II) can be used to stereospecifically couple a suitably protected nucleoside (or even a suitably protected oligonucleotide) to an oligonucleotide. Thus, the N-acylphosphoramidite of the present invention can be attached to an oligomer such as, for example, an oligonucleotide (i.e., wherein Q is an oligonucleotide), as well as a monomer (i.e., wherein Q is a nucleoside). The nucleophile which is coupled to an N-acylphosphoramidite of the present invention also can be monomeric or oligomeric.

Accordingly, $Q^1$ also includes oligomers that contain, as a component thereof, a nucleoside substituent as described herein.

The C=X bond of the N-acylphosphoramidites of the present invention includes carbonyl and carbonyl equivalents. Thus, the N-acyl group includes carbonyl (wherein X is O), thiocarbonyl (wherein X is S), and selenocarbonyl (wherein X is Se). Typically, the N-acyl group is a carbonyl, wherein X is O.

Examples of monomeric compounds of the present invention include compounds of the formulae:

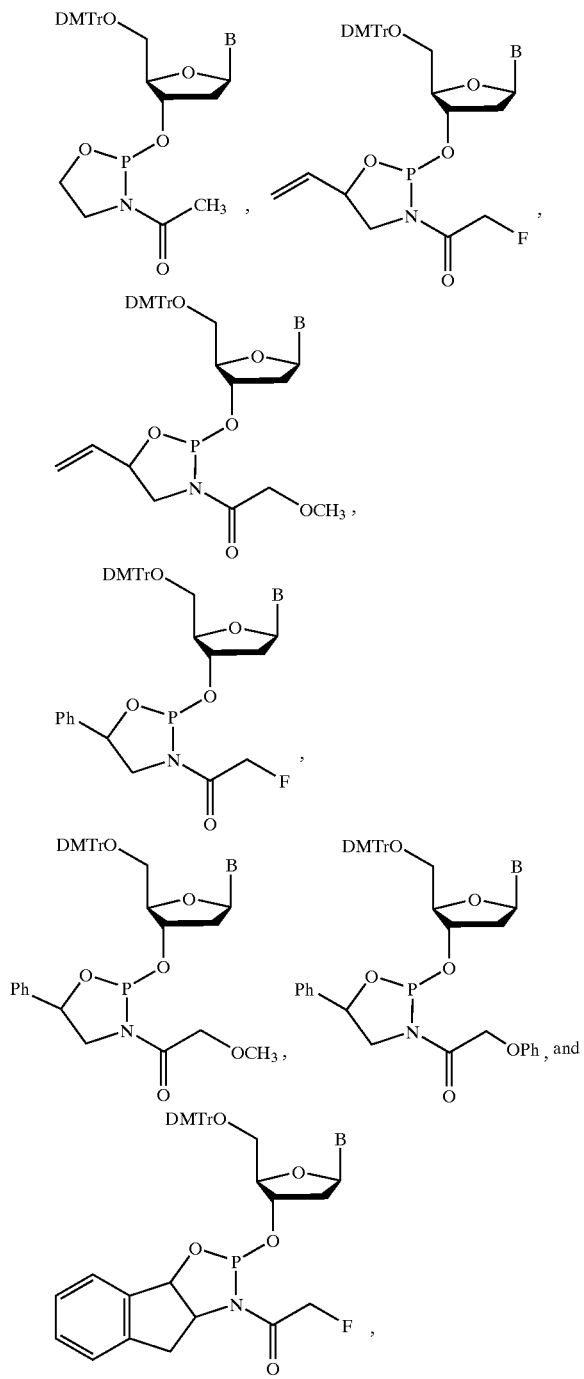

wherein B is as defined herein.

Stereospecific coupling reactions can be carried out successively "n" times, for example, starting with a nucleophile $R^4$—O—$Q^1$—OH (wherein $R^4$ and $Q^1$ are as defined herein), and continuing thereafter, to provide an intermediate of formula (III), wherein n is an integer from 1 to about 300. It will be appreciated that when a compound of formula (I) is reacted with a nucleophile $R^4$—O—$Q^1$—OH, then "$R^4$" of formula (I) is represented by "$R^{15}$" of formula (III). When the protecting group $R^{15}$ is removed, then $R^{15}$ becomes a hydrogen. $R^4$ and $R^{15}$ desirably are not both solid supports in formula (III). When $R^{15}$ is hydrogen, then another coupling reaction can be carried out, and the process repeated successively, until a polymer of desired length or structure is obtained. In each successive reaction, the Q substituent of formula (I) can be the same or different, as desired, to obtain a variety of different combinations. As such, Q can be the same or different in each of the units defined by n, when n is greater than 1. Preferably, n is in the range of from about 3 to about 200; more preferably, n is in the range from about 10 to about 40; and most preferably n is in the range from about 15 to about 25.

In a preferred embodiment, Q and/or $Q^1$ is a nucleoside substituent of the formula:

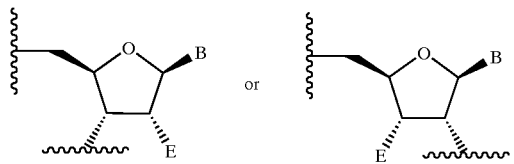

In this embodiment, $R^4$ is advantageously a solid support or a protecting group. The protecting group is most preferably a 4,4'-dimethoxytrityl protecting group.

As utilized herein, the term "alkyl" means a straight-chain or branched-chain alkyl radical which, unless otherwise specified, contains from about 1 to about 20 carbon atoms, preferably from about 1 to about 10 carbon atoms, more preferably from about 1 to about 8 carbon atoms, and most preferably from about 1 to about 6 carbon atoms. Examples of such alkyl radicals include methyl, ethyl, propyl, isopropyl, n-butyl, sec-butyl, isobutyl, tert-butyl, pentyl, isoamyl, hexyl, octyl, dodecanyl, and the like.

The term "alkenyl" means a straight-chain or branched-chain alkenyl radical, which has one or more double bonds and, unless otherwise specified, contains from about 2 to about 20 carbon atoms, preferably from about 2 to about 10 carbon atoms, more preferably from about 2 to about 8 carbon atoms, and most preferably from about 2 to about 6 carbon atoms. Examples of alkenyl radicals include vinyl, allyl, 1,4-butadienyl, isopropenyl, and the like.

The term "alkynyl" means a straight-chain or branched-chain alkynyl radical, which has one or more triple bonds and contains from about 2 to about 20 carbon atoms, preferably from about 2 to about 10 carbon atoms, more preferably from about 2 to about 8 carbon atoms, and most preferably from about 2 to about 6 carbon atoms. Examples of alkynyl radicals include ethynyl, propynyl (propargyl), butynyl, and the like.

The terms "alkylamino" and "dialkylamino" mean an alkyl or a dialkyl amine radical, wherein the term "alkyl" is defined as above. Examples of alkylamino radicals include methylamino ($NHCH_3$), ethylamino ($NHCH_2CH_3$), n-propylamino, isopropylamino, n-butylamino, isobutylamino, sec-butylamino, tert-butylamino, n-hexylamino, and the like. Examples of dialkylamino radicals include dimethylamino ($N(CH_3)_2$), diethylamino ($N(CH_2CH_3)_2$), di-n-propylamino, diisopropylamino, di-n-butylamino, diisobutylamino, di-sec-butylamino, di-tert-butylamino, di-n-hexylamino, and the like.

The term "cycloalkyl" means a monocyclic alkyl radical, or a polycyclic alkyl which comprises one or more alkyl carbocyclic rings, which can be the same or different when the polycyclic radical has 3 to about 10 carbon atoms in the carbocyclic skeleton of each ring. Preferably, the cycloalkyl has from about 4 to about 7 carbon atoms, more preferably from about 5 to about 6 carbons atoms. Examples of monocyclic cycloalkyl radicals include cyclopropyl, cyclobutyl, cyclopentyl, cyclohexyl, cycloheptyl, cyclodecyl, and the like. Examples of polycyclic cycloalkyl radicals include decahydronaphthyl, bicyclo[5.4.0]undecyl, adamantyl, and the like.

The term "aryl" refers to an aromatic carbocyclic radical, as commonly understood in the art, and includes monocyclic and polycyclic aromatics such as, for example, phenyl and naphthyl radicals, which radicals are, unless indicated otherwise, unsubstituted or substituted with one or more substituents selected from the group consisting of a halogen, an alkyl, an alkoxy, an amino, a cyano, a nitro, and the like. Preferably, the aryl has one or more six-membered carbocyclic rings including, for example, phenyl, naphthyl, and biphenyl, and are unsubstituted or substituted as set forth herein.

The term "aralkyl" means alkyl as defined herein, wherein an alkyl hydrogen atom is replaced by an aryl as defined herein. Examples of aralkyl radicals include benzyl, phenethyl, 1-phenylpropyl, 2-phenylpropyl, 3-phenylpropyl, 1-naphthylpropyl, 2-naphthylpropyl, 3-naphthylpropyl, 3-naphthylbutyl, and the like.

The terms heterocycle and heterocyclic refer to both heterocycloalkyls and heteroaryls. The term "heterocycloalkyl" means a cycloalkyl radical as defined herein (including polycyclics), wherein at least one carbon of a carbocyclic ring is substituted with a heteroatom such as, for example, O, N, or S. The heterocycloalkyl optionally has one or more double bonds within a ring, and may be aromatic, but is not necessarily aromatic. The heterocycloalkyl preferably has 3 to about 10 atoms (members) in the carbocyclic skeleton of each ring, preferably from about 4 to about 7 atoms, more preferably from about 5 to about 6 atoms. Examples of heterocycloalkyl radicals include epoxy, aziridyl, oxetanyl, tetrahydrofuranyl, ribose, dihydrofuranyl, piperidinyl, piperazinyl, pyranyl, morpholinyl, and the like.

The term "heteroaryl" means a radical defined by an aromatic heterocyclic ring as commonly understood in the art, including monocyclic radicals such as, for example, imidazole, thiazole, pyrazole, pyrrole, furane, pyrazoline, thiophene, oxazole, isoxazole, pyridine, pyridone, pyrimidine, cytosine, 5-methylcytosine, thymine, pyrazine, and triazine radicals, and polycyclics such as, for example, quinoline, isoquinoline, indole, purine, adenine, guanine, $N^6$-methyladenine, and benzothiazole radicals, which heteroaryl radicals are unsubstituted or substituted with one or more substituents, which are the same or different, selected from the group consisting of a halogen, an alkyl, an alkoxy, an amino, a cyano, a nitro, and the like. It will be appreciated that the heterocycloalkyl and the heteroaryl substituents can be coupled to the compounds of the present invention via a heteroatom, such as nitrogen (e.g., 1-imidazolyl). It will also be appreciated that heteroaryls, as defined herein, are not necessarily "aromatic" in the same context as phenyl is aromatic, although heteroaryls nonetheless demonstrate physical and chemical properties associated with aromaticity, as the term is understood in the art.

The term "nucleoside" includes all modified and naturally occurring nucleosides, including all forms of furanosides found in nucleic acids. Naturally occurring nucleosides include, for example, adenosine, guanosine, cytidine, thymidine, and uridine.

Nucleoside "derivatives" or "analogs" include synthetic nucleosides as described herein. Nucleoside derivatives also include nucleosides having modified base moieties, with or without protecting groups. Such analogs include, for example, deoxyinosine, 2,6-diaminopurine-2'-deoxyriboside, 5-methyl-2'-deoxycytidine, and the like. The base rings most commonly found in naturally occurring nucleosides are purine and pyrimidine rings. Naturally occurring purine rings include, for example, adenine, guanine, and $N^6$-methyladenine. Naturally occurring purine rings include, for example, cytosine, thymine, and 5-methylcytosine. The compounds and methods of the present invention include such base rings and synthetic analogs thereof, as well as unnatural heterocycle-substituted base sugars, and even acyclic substituted base sugars. Moreover, nucleoside derivatives include other purine and pyrimidine derivatives, for example, halogen-substituted purines (e.g., 6-fluoropurine), halogen-substituted pyrimidines, $N^6$-ethyladenine, $N^6$-(alkyl)-cytosines, 5-ethylcytosine, and the like.

The term "oligonucleotide" as used herein includes linear oligomers of natural or modified nucleosides, and modified ologonucleotides, as described herein. Oligonucleotides include deoxyribonucleosides, ribonucleosides and anomeric forms thereof, and the like. Oligonucleotides are typically linked by phoshodiester bonds, or the equivalent thereof, ranging in size from a few monomeric units (e.g., 3 or 4) to several hundred monomeric units. Preferably, the oligonucleotides of the present invention are oligomers of naturally-occurring nucleosides ranging in length from about 12 to about 60 monomeric units, and more preferably, from about 15 to about 30 monomeric units. Whenever an oligonucleotide is represented by a sequence of letters, such as "AGTC" it will be appreciated that the nucleotides are in the 5'-3' orientation from left to right.

Phosphorus linkages between nucleosidic monomers include phosphodiester bonds and analogs of phosphodiester bonds, such as phoshorothioate, phosphoroselenoate, alkylphosphonate, and phosphoramidate. Preferably, the monomers of the oligonucleotides of the present invention are linked by phosphodiester, phosphorothioate, methanephosphonate, or phosphoramidate linkages.

The term "oligomer comprising a nucleoside" as utilized herein means an oligomer in which at least one of the monomeric units comprises nucleoside, and at least one of the other monomeric units is not a nucleoside. For example, one of the monomeric units in the oligomer can be an amino acid, an organic spacer (e.g., an aliphatic or aromatic spacer, an alkylene glycol, or the like), or a carbohydrate (e.g., a sugar). Moreover, one of the non-nucleoside units of the oligomer can itself be oligomeric, for example, a peptide, an oligosaccharide, a polyalkylene glycol, or the like.

Any suitable protecting group (sometimes referred to as a blocking group) can be utilized in accordance with the present invention. The term "protecting group" as used herein means a substituent, a functional group, a salt, a ligand, or the like, which is bonded (e.g., via covalent bond, ionic bond, or complex) to a potentially reactive functional group and prevents the potentially reactive functional group from reacting under certain reaction conditions. Potentially reactive functional groups include, for example, amines, carboxylic acids, alcohols, double bonds, and the like. Preferably, the protecting group is stable under the reaction conditions for which the protecting group is employed, and also can be removed under reasonably mild deprotection conditions. It will be appreciated that the protecting group to be used in accordance with the present invention depends on the type of substituent that is being protected. Thus, it is not uncommon to use a different protecting group for each of a phosphite oxygen, a phosphate oxygen, an amine, a thiol, a hydroxyl, and the like. It will also be appreciated that the choice of protecting groups will depend on other factors such as, for example, the reaction conditions employed in a particular synthetic step, the pH, the temperature, and the relative reactivities of the reactants and/or products.

Protecting groups for hydroxyls include, for example, silyl ethers (e.g., trimethylsilyl, triethylsilyl, tert-butyldimethylsilyl, dimethylphenylsilyl, and diphenylmethylsilyl), benzyl carbonates, trityl, monomethoxytrityl, dimethoxytrityl, esters (e.g., acetate, benzoate, and the like), pixyl, tert-butyloxycarbonyl, 9-fluorenylmethyloxycarbonyl (Fmoc), a tetrahydropyranyl group, and the like. When the hydroxyl is a sugar hydroxyl, preferred protecting groups include, for example, pixyl, acetyl, 9-fluorenylmethyloxycarbonyl (Fmoc), t-butyldimethylsilyl (TBDMS), trityl, monomethoxytrityl ("MMT" or "MMTr"), dimethoxytrityl ("DMT" or "DMTr"), and the like.

Protecting groups for nitrogen include, for example, amides (e.g., trifluoroacetyl, benzoyl, and isobutyryl), carbamates (e.g., tert-butyloxycarbonyl and N-benzyloxycarbonyl), trityl, and the like. When an amine to be protected is part of a nucleoside base ring, suitable protecting groups can include amides, for example, benzoyl, isobutyryl, and the like.

The term "carboxyl" means any functional group with a carbonyl backbone, and includes functional groups such as, for example, a carboxylic acid, an esters (e.g., ethoxycarbonyl), and amides (e.g., benzamido).

Any suitable solid support can be used in the compounds and methods of the present invention. Solid supports are commonly known in the art and include, for example, organic solid supports (e.g., crosslinked polystyrene) and inorganic solid supports. Preferably, the solid support is inorganic, and is more preferably a silica support. It will be appreciated that the solid support includes all linkers, spacers, arms, and other moieties (organic or inorganic) known in the art for manipulating attachment to a solid support. It will also be appreciated that the solid support can be bonded to the molecule directly, without using any of the aforesaid linkers, spacers, arms, or other connecting moieties.

Some aspects of the invention are common with known approaches to solid phase synthesis of oligonucleotides, for example, selection of suitable protecting groups, selection of suitable solid phase supports, and the like. Consequently, considerable guidance in making such selections in the context of the present invention can be found in literature, e.g. Beaucage et al., *Tetrahedron*, 49, 6123–6194 (1993).

Typically, the monomeric units in the polymers prepared in accordance with the present invention are connected via phosphorus diester linkages, for example, phosphate or chiral phosphate (P-chiral) linkages, as desired. However, the compounds and methods of the present invention are not limited to the synthesis of polymers having only phosphorus-linked monomeric units. For example, the compounds of the present invention also can be used to introduce one or more phosphorus-linked units into a polymer having another type of linkage in the structure thereof, for example, a carbonate, a urea, an ester, an ether, or any suitable combination thereof.

In a preferred embodiment, the compound of the present invention is a cyclic N-acylphosphoramidite of the formula:

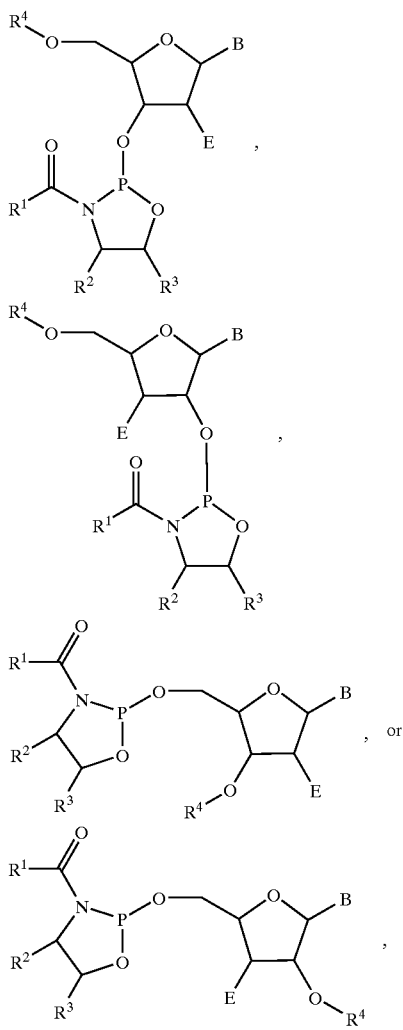

wherein R¹–R⁴, B, and E are as defined herein.

Particular substituents for $R^1$, $R^2$, $R^{2'}$, $R^3$ and/or $R^{3'}$ (formulae (I) or (III)), or $R^6$ (formula (II)) can be selected which have a structure that facilitates removal of the organic moiety remaining on the non-bridging phosphate or phosphorothioate oxygen after coupling has been carried out in accordance with the present invention. For example, $R^1$ advantageously can be an alkyl group substituted with a suitably positioned nucleophile that is protected with an easily removable protecting group (e.g., a "latent" internal nucleophile). When the nucleophile is released upon deprotection, the nucleophile on $R^1$ is positioned such that it can intramolecularly attack (and therefore cleave) the bond linking the organic moiety to the non-bridging phosphate, phosphorothioate or phosphoroselenoate oxygen. For example, when $R^1$ is trifluoroacetamido, the trifluoroacetyl group can be easily removed, thereby liberating an amine (nucleophile) which, in turn, intramolecularly cleaves the organic moiety from the non-bridging phosphate, phosphorothioate or phosphoroselenoate oxygen as illustrated below in Scheme 1.

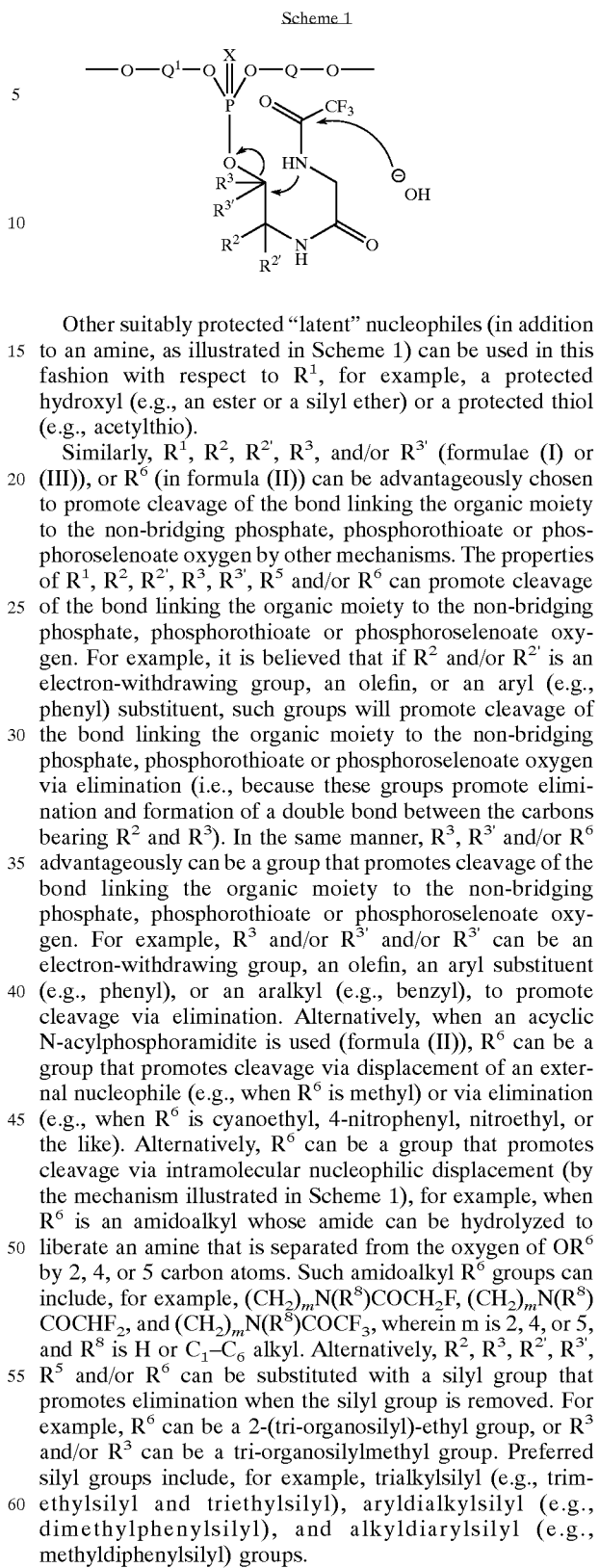

Scheme 1

Other suitably protected "latent" nucleophiles (in addition to an amine, as illustrated in Scheme 1) can be used in this fashion with respect to $R^1$, for example, a protected hydroxyl (e.g., an ester or a silyl ether) or a protected thiol (e.g., acetylthio).

Similarly, $R^1$, $R^2$, $R^{2'}$, $R^3$, and/or $R^{3'}$ (formulae (I) or (III)), or $R^6$ (in formula (II)) can be advantageously chosen to promote cleavage of the bond linking the organic moiety to the non-bridging phosphate, phosphorothioate or phosphoroselenoate oxygen by other mechanisms. The properties of $R^1$, $R^2$, $R^{2'}$, $R^3$, $R^{3'}$, $R^5$ and/or $R^6$ can promote cleavage of the bond linking the organic moiety to the non-bridging phosphate, phosphorothioate or phosphoroselenoate oxygen. For example, it is believed that if $R^2$ and/or $R^{2'}$ is an electron-withdrawing group, an olefin, or an aryl (e.g., phenyl) substituent, such groups will promote cleavage of the bond linking the organic moiety to the non-bridging phosphate, phosphorothioate or phosphoroselenoate oxygen via elimination (i.e., because these groups promote elimination and formation of a double bond between the carbons bearing $R^2$ and $R^3$). In the same manner, $R^3$, $R^{3'}$ and/or $R^6$ advantageously can be a group that promotes cleavage of the bond linking the organic moiety to the non-bridging phosphate, phosphorothioate or phosphoroselenoate oxygen. For example, $R^3$ and/or $R^{3'}$ and/or $R^{3'}$ can be an electron-withdrawing group, an olefin, an aryl substituent (e.g., phenyl), or an aralkyl (e.g., benzyl), to promote cleavage via elimination. Alternatively, when an acyclic N-acylphosphoramidite is used (formula (II)), $R^6$ can be a group that promotes cleavage via displacement of an external nucleophile (e.g., when $R^6$ is methyl) or via elimination (e.g., when $R^6$ is cyanoethyl, 4-nitrophenyl, nitroethyl, or the like). Alternatively, $R^6$ can be a group that promotes cleavage via intramolecular nucleophilic displacement (by the mechanism illustrated in Scheme 1), for example, when $R^6$ is an amidoalkyl whose amide can be hydrolyzed to liberate an amine that is separated from the oxygen of $OR^6$ by 2, 4, or 5 carbon atoms. Such amidoalkyl $R^6$ groups can include, for example, $(CH_2)_m N(R^8) COCH_2F$, $(CH_2)_m N(R^8) COCHF_2$, and $(CH_2)_m N(R^8) COCF_3$, wherein m is 2, 4, or 5, and $R^8$ is H or $C_1$–$C_6$ alkyl. Alternatively, $R^2$, $R^3$, $R^{2'}$, $R^{3'}$, $R^5$ and/or $R^6$ can be substituted with a silyl group that promotes elimination when the silyl group is removed. For example, $R^6$ can be a 2-(tri-organosilyl)-ethyl group, or $R^3$ and/or $R^3$ can be a tri-organosilylmethyl group. Preferred silyl groups include, for example, trialkylsilyl (e.g., trimethylsilyl and triethylsilyl), aryldialkylsilyl (e.g., dimethylphenylsilyl), and alkyldiarylsilyl (e.g., methyldiphenylsilyl) groups.

Alternatively, $R^1$, $R^2$, $R^{2'}$, $R^3$ and/or $R^{3'}$ (formulae (I) or (III)), or $R^5$ or $R^6$ (formula (II)), can be chosen to promote thermal cleavage of the bond linking the organic moiety to the non-bridging phosphate, phosphorothioate or phosphoroselenoate oxygen. Cleavage of the bond linking the organic moiety to the non-bridging phosphate, phosphorothioate or phosphoroselenoate oxygen is indicated by the dotted lines shown in FIGS. 13A and 13B. Thermal cleavage can be advantageous in that the use of harsh chemicals, such as ammonium hydroxide, is avoided. As such, thermal cleavage provides a mild alternative that can be desirable for use in monomeric, oligomeric, or polymeric compounds with chemically labile substituents. It will be appreciated that certain combinations or structural features of $R^1$, $R^2$, $R^{2'}$, $R^3$, and $R^{3'}$, or of $R^1$, $R^5$, or $R^6$, can be chosen to promote thermal cleavage of the bond linking the organic moiety to the non-bridging phosphate, phosphorothioate or phosphoroselenoate oxygen. For example, $R^3$ can be a substituent that makes the bond linking the organic moiety to the non-bridging phosphate, phosphorothioate or phosphoroselenoate oxygen more labile, e.g., an electron withdrawing group or a cation-stabilizing group, e.g., an aryl, preferably a phenyl. Alternatively, $R^3$ and/or $R^{3'}$ can be a substituent that makes the carbon to which it is attached less hindered (e.g., $R^3$ and $R^{3'}$ are H) and more susceptible to internal thermal displacement by the C=X residue.

Figure 13A:
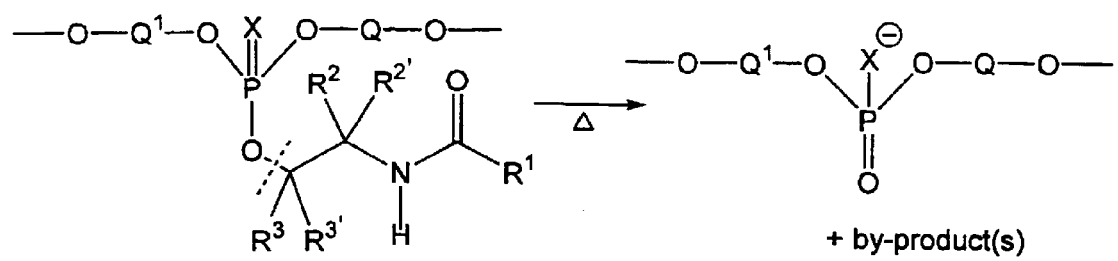
FIG. 13A illustrates a general example of a thermal cleavage of the bond linking an organic moiety to a non-bridging phosphate or phosphorothioate oxygen.
Figure 13B:
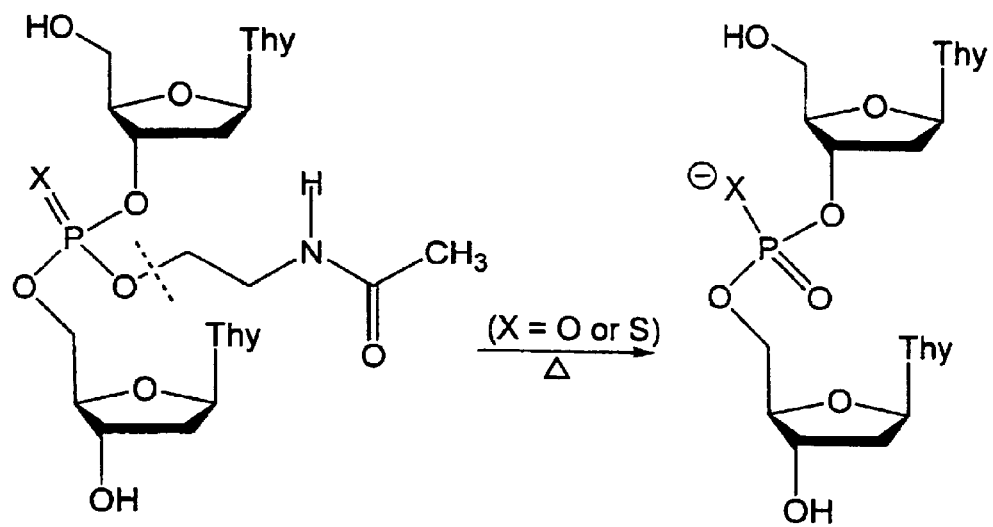
FIG. 13B illustrates specific examples thermal cleavage of the bond linking an organic moiety to a non-bridging phosphate or phosphorothioate oxygen.

An example of such a thermal cleavage is generally illustrated in FIG. 13A. Specific examples of thermal cleavage are shown in FIG. 13B. In one embodiment, $R^1$ is an alkyl, $R^2$, $R^{2'}$, and $R^{3'}$ all are H, and $R^3$ is H or an aryl. In a preferred combination, $R^1$ is methyl, $R^{2'}$ and $R^{3'}$ are H, and $R^3$ is H or phenyl. In a particularly preferred combination, $R^1$ is methyl, and $R^2$, $R^{2'}$, $R^3$ and $R^{3'}$ all are H (e.g., as shown in FIG. 13B). When $R^1$ is methyl, and $R^2$, $R^3$, $R^{2'}$ and $R^{3'}$ are H, thermal cleavage of the bond linking the organic moiety to the non-bridging phosphate, phosphorothioate or phosphoroselenoate oxygen can be accomplished under fairly mild conditions. For example, thermal cleavage in the two systems shown in FIG. 13B (i.e., wherein X is O or S) can be carried out to completion in about 80 minutes at about 80° C.

The present invention further provides a method of preparing a polymer, including the steps of:
(a) reacting a nucleophile that can displace the N-acyl group of an N-acylphosphoramidite of formula (I) or (II), wherein $R^4$ is a protecting group with an N-acylphosphoramidite of formula (I) or (II), preferably in the presence of a base, to produce an adduct of the N-acylphosphoramidite and the nucleophile, the adduct comprising a tricoordinated phosphorus atom;
(b) reacting the adduct with a reagent selected from the group consisting of oxidizing agents, sulfurizing agents, and selenizing agents, to produce a product, wherein the tricoordinated phosphorus atom is converted into a phosphorus atom with a valence of greater than three (e.g., a tetracoordinated phosphorous atom); and
(c) removing the protecting group $R^4$ from the product.

Optionally, steps (a) through (c) can be repeated, one or more times as necessary, until a polymer of specified length is obtained.

Desirably, the method of the present invention further comprises the step of the bond linking the organic moiety to the non-bridging phosphate, phosphorothioate or phosphoroselenoate oxygen atom (e.g., by aminolysis or thermal cleavage), after step (a), (b)* (c) or (d). While cleavage of the bond linking the organic moiety to the non-bridging phosphate, phoshphorothioate or phosphoroselenoate oxygen atom can be done at any stage after any of steps (a)–(d), it is preferably carried out after step (c) or (d). Most preferably, the bond linking the organic moiety to the non-bridging phosphate, phoshphorothioate or phosphoroselenoate oxygen atom is cleaved thermally, for example, as illustrated in FIGS. 13A and 13B.

The N-acylphosphoramidite used in step (a) is a compound of formula (I) or (II), wherein $R^4$ is a protecting group. Preferably, the N-acylphosphoramidite is a P-chiral N-acylphosphoramidite. When a P-chiral N-acylphosphoramidite is used, the resulting adduct also is P-chiral, since the coupling reaction (step (a)) occurs with stereospecificity. Moreover, reaction of the resulting adduct of step (a) with an oxidizing, a sulfurizing, or a selenizing agent (step (b)) occurs stereospecifically, that is, without any epimerization at phosphorus. For example, sulfurization of the P-diastereomerically pure adduct of step (a), obtained by using a P-diastereomerically pure N-acylphosphoramidite, results in a P-diastereomerically pure adduct. Although sulfurization reactions are applied to adducts prepared from standard phosphoramidite coupling chemistry, the phosphorothioate products obtained thereby contain a mixture of phosphorus stereoisomers (i.e., they are not stereopure) because the phosphorus adducts prepared via standard phosphoramidite chemistry contain a mixture of stereoisomers. As indicated above, standard phosphoramidite coupling reactions are not stereospecific. Thus, the present invention stereospecifically produces P-chiral coupling adducts and, thus, provides access to oligonucleotides which are stereochemically pure at phosphorus (e.g., oligonucleotide phosphorothioates).

Any suitable base can be used in coupling step (a) including, for example, inorganic and organic bases. Preferably, the base used in step (a) is a relatively non-nucleophilic base, which is more preferably a relatively non-nucleophilic amine base such as, for example, tetramethylguanidine (TMG). Advantageously, and preferably, the coupling conditions of the present invention are carried out under basic conditions. As a result, the use of an acid in the coupling reaction is avoided, and the P-diastereomerically pure adduct formed in step (a) does not epimerize. Since the coupling reaction of step (a) occurs with complete stereospecificity, the stereochemical purity with respect to phosphorus can be governed by the stereochemical purity of the N-acylphosphoramidite used therein.

Desirably, the method of the present invention further includes the step of capping the unreacted nucleophilic group after step (b) or (c). Capping is usually done as a prophylactic measure to prevent the unreacted nucleophilic groups, left over from prior condensation reactions, from reacting in subsequent condensation cycles. Capping promotes synthetic advantages such as, for example, preventing the formation of undesirable side products. When the nucleophile (or oligomeric adduct, if steps (a)–(c) are repeated at least once) is a sugar hydroxyl, capping typically involves acylation of the unreacted sugar hydroxyls.

Typically, the reaction in step (a) leads to formation of a tricoordinated P-chiral product, thereby enabling, in step (b), the formation of a P-chiral product. Deprotection of the preferred tetracoordinated P-chiral products can provide a P-chiral polymer of predetermined chirality and length. Preferably, the nucleophile utilized in the method of the present invention is a nucleoside, an oligonucleotide, or a derivative thereof, step (a) utilizes a P-chiral N-acylphosphoramidite, and step (b) comprises sulfurization. Repeating the steps (a)–(c) can be continued as many times as desired, until a polymer of a particular length and chirality is obtained.

As discussed above, formation of a tricoordinated P-chiral product in step (a) can be achieved by using any suitable P-chiral N-acylphosphoramidite, most preferably a P-chiral analog of compound (I) or (II). In accordance with the present invention, P-chiral N-acylphosphoramidites can be obtained by any suitable method such as, for example, chiral synthesis, chromatographic resolution, or any suitable combination thereof. Chromatographic separation of a mixture of P-chiral isomers can be facilitated, for example, if the monomeric subunit of the N-acylphosphoramidite is a chiral molecule, as illustrated, for example, in Scheme 2.

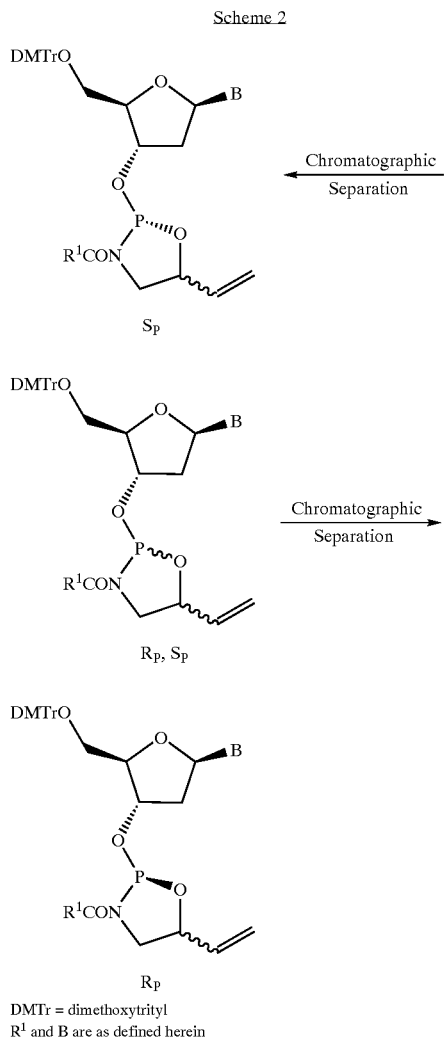

DMTr = dimethoxytrityl
$R^1$ and B are as defined herein

Using this technique, P-chiral products having any desired phosphorus stereochemistries can be stereospecifically prepared simply by selecting the appropriate P-chiral N-acylphosphoramidite and using it in accordance with the method of the present invention.

The present invention provides new chemistry for synthesizing oligonucleotides and related polymers having phosphate or phosphate analogue linkages. In particular, whenever phosphate analogue linkages are P-chiral, the present invention provides a method for synthesizing polymers having a predetermined sequence of P-chirality along the polymer backbone. P-chiral oligonucleotides obtained by the method of the present invention can be employed as hybridization probes, therapeutic agents, e.g., selective protein expression inhibitors, and the like.

The methods and compounds of the present invention offer other unique advantages, such as moisture stability. In particular, the N-acylphosphoramidites of the present invention are far more stable to moisture under the coupling conditions of step (a) than are the conventional phosphoramidite synthons for which mild acid conditions are required. Moisture instability is a major disadvantage inherent in oligonucleotide synthesis using standard phosphoramidite chemistry. In particular, standard phosphoramidite precursors hydrolytically degrade, rapidly, upon contact with moisture under standard (acidic) conditions which are required to accomplish a coupling reaction. As such, acid-promoted phosphoramidite nucleoside couplings typically are carried out in a scrupulously moisture-free environment, particularly if the target polymer comprises a large number of monomeric units. The requirement of maintaining an essentially water-free environment dramatically increases the cost and complexity oligonucleotide synthesis using standard phosphoramidite chemistry. Since the N-acylphosphoramidites of the present invention undergo hydrolytic degradation sluggishly, or not at all, under the coupling conditions of step (a), the problem of competitive hydrolytic cleavage has essentially been eliminated. As such, the method of the present invention need not be carried out in a scrupulously water-free environment.

In a preferred embodiment, the nucleophile is attached to a solid support. Accordingly, the present invention provides a novel approach to solid phase synthesis, in particular, the synthesis of oligonucleotides and related polymers, using N-acylphosphoramidites, for example, hydroxyl-protected monomeric-O-(O-protected)-(N-acyl)phosphoramidites.

When the nucleophile is attached to a solid support, the nucleophile is preferably a compound of the formula:

$R^4$—O—Q—OH wherein Q is a nucleoside, an oligonucleotide comprising a nucleoside, or an oligomer comprising a nucleoside, wherein the nucleoside is of the formula:

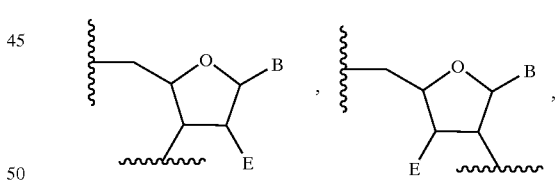

wherein B and E are as defined herein, or an oligomer which includes one of these nucleosides as a component thereof, and $R^4$ is the solid support.

Desirably, the nucleophile is a monomer. In a preferred embodiment, the nucleophile is a monomer and is attached to a solid phase support through a linking group that will resist cleavage in the presence of a base, for example, a base used in step (a), thereby allowing the resulting oligomer/polymer to remain attached to the solid support throughout each successive coupling step. When a solid support is used in connection with a nucleophile (e.g., a nucleophilic monomer), Q is preferably a nucleoside of the formula:

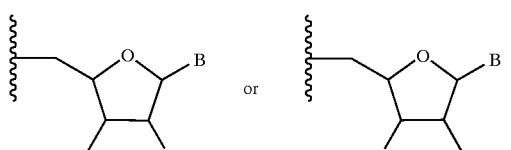

wherein B and E are as defined herein. In one preferred embodiment, Q is a nucleoside substituent having a defined stereochemistry, and is represented by the formula:

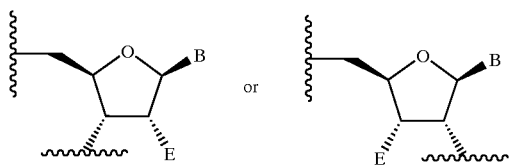

wherein B and E are as defined herein.

In a particularly preferred embodiment, a cyclic N-acylphosphoramidite of formula (I) is used to effect the desired coupling, and is represented by the formula:

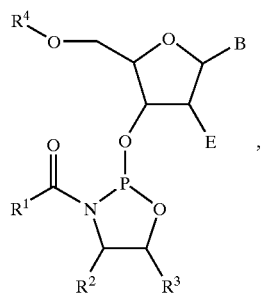

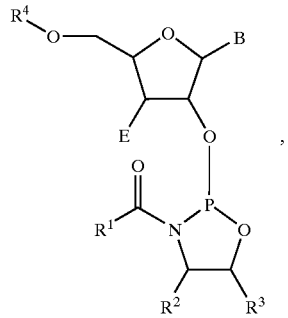

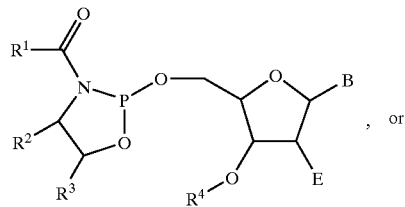, or

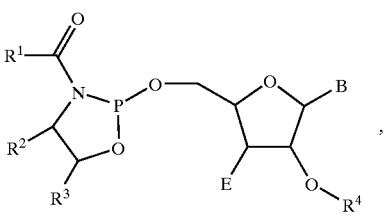

wherein $R^1$–$R^4$, B, and E are as defined herein. Preferably, B is a purine, a pyrimidine, adenine, guanine, cytosine, uracil, or thymine, wherein B is unsubstituted or substituted with one or more substituents, which are the same or different, selected from the group consisting of a protecting group, $R^{11}$, $OR^{11}$, $NHR^{11}$, $NR^{11}R^{12}$, CN, $NO_2$, $N_3$, and a halogen, wherein $R^{11}$ and $R^{12}$ are as defined herein.

In one preferred embodiment, $R^1$ is an alkyl, which is unsubstituted or substituted with one or more substituents selected from the group consisting of fluorine, $OR^7$ and $SR^7$, wherein $R^7$ is an alkyl or an aryl. More preferably, $R^1$ is a $C_1$–$C_6$ alkyl, which is unsubstituted or substituted with one or more fluorine atoms. Still more preferably, $R^1$ is a methyl, which is unsubstituted or substituted with one or more fluorine atoms, and is most preferably fluoromethyl.

In another preferred embodiment, $R^2$, $R^{2'}$, $R^3$, or $R^{3'}$ is a vinyl group, a phenyl or a benzyl. In still another preferred embodiment, $R^4$ is a 4,4'-dimethoxytrityl group.

Oxidizing agents that can be used in the context of the present invention include any suitable reagent that can oxidize a tricoordinated phosphorus atom, particularly a phosphite, to provide a phosphorus atom having a valence of higher than three, preferably a tetracoordinated phosphorus atom such as, for example, a phosphate, or an equivalent thereof. Suitable oxidizing agents include, for example, $I_2/H_2O$, peroxides, such as tert-butylhydroperoxide, and the like.

Sulfurizing agents include any suitable reagent that can sulfurize a tricoordinated phosphorus atom, particularly a phosphite, to provide a phosphorus atom with a valence of greater than three, preferably a tetracoordinated phosphorus atom such as, for example, a phosphorothioate, or an equivalent thereof. Suitable sulfurizing agents include, for example, 3H-1,2-benzodithiol-3-one 1,1-dioxide ("Beaucage Reagent"), phenylacetyl disulfide, bis(O,O-diisopropoxyphosphinothioyl) disulfide, and the like.

Selenizing agents include any suitable reagent that can selenize a tricoordinated phosphorus atom, particularly a phosphite, to provide a phosphorus atom having a valence of greater than three, preferably a tetracoordinated phosphorus atom such as a phosphoroselenoate, or an equivalent thereof. Suitable selenizing agents include, for example, potassium selenocyanate (KSeCN) or elemental selenium.

The present invention also provides an alternative method to the synthesis of unmodified oligonucleotides and to the non-stereospecific synthesis of oligonucleotide analogues. The alternative method of the present invention comprises:

(i) providing a nucleophile;
(ii) reacting the nucleophile, in the presence of a mild acid, with a synthon of the formula:

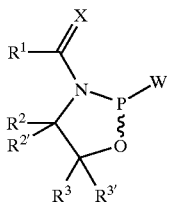

wherein X and $R^1$–$R^3$ are as defined herein, and W is a leaving group amenable to nucleophilic displacement, to produce an adduct of the nucleophile and the synthon, which is an N-acylphosphoramidite having a tricoordinated phosphorus atom;

(iii) reacting, in the presence of a base, the resulting adduct with a nucleoside, having at least one nucleophilic group and at least one suitably protected nucleophilic group, to produce a product;

(iv) deprotecting the protected nucleophilic group of the resulting product;

(v) oxidatively transforming the tricoordinated phosphorus atom into a tetracoordinated one; and (vi) repeating the steps (ii)–(v) until an oligomer or polymer of predetermined length is obtained.

Preferably, the method further comprises the step of capping unreacted nucleophilic groups after step (iv) or (v), as discussed herein. It is further preferred to attach the first monomer (i.e., the nucleophile in the first coupling reaction of a synthesis) to a solid phase support through a linking group that will resist cleavage, when in the presence of the base used in step (iv).

It is preferred that W is a leaving group that can be displaced by a monomer of the formula $R^4$—O—Q-OH or $R^4$—O—$Q^1$—OH, wherein $R^4$, Q, and $Q^1$ are as defined herein. In a preferred embodiment, W is halogen, a dialkylamino having from 2 to about 8 carbon atoms (e.g., dimethylamino, diethylamino, N-methyl-N-isopropylamino, and the like), or a cyclic amine substituent having from 2 to about 6 carbon atoms (e.g., pyrrolidinyl, piperidinyl, morpholinyl, aziridinyl, and the like), wherein one or more carbon atoms of the dialkylamino and cyclic amine substituents are unsubstituted or substituted with one or more heteroatoms, which are the same or different. More preferably W is Cl, dialkylamino, or a cyclic amino. Most preferably, W is diethylamino.

The reactions in steps (iii) and (iv) enable the formation of the tricoordinated P-chiral product and, preferably, step (v) causes formation of the tetracoordinated P-chiral product in a stereospecific manner. Moreover, further deprotection preferably gives either a P-achiral or a P-chiral polymer of predetermined length. In step (iv), suitably protected nucleosides comprise unmodified and/or modified nucleosides. Step (v) preferably comprises oxidation and/or sulfurization.

In either method of the present invention, it is preferred that an N-acylphosphoramidite of formula (I) is used. Thus, in a preferred embodiment, the resulting product of steps (a)–(c), (a)–(d), (iii), or (iii)–(v) is a compound of formula (III). Compounds of formula (III) are dimeric, when one coupling step is performed (n=1). However, any desired number of subsequent coupling steps can be performed, typically requiring deprotection (step (c) or step (iv)) prior to subsequent coupling reactions, wherein each monomeric unit defined by "n" is the same or different, and the substituents $R^1$–$R^4$, $R^{15}$, X, $Q^1$, and Q are as defined herein. Compounds of formula (III) are useful in the synthesis of polymers, particularly phosphodiester-linked polymers, more particularly P-chiral phosphodiester-linked polymers, which can be obtained from (III) via cleavage of the 2-amidoethoxy fragment (i.e., the bond linking the organic moiety to the non-bridging phosphate, phosphorothioate or phosphoroselenoate oxygen atom), as described herein.

Oligomers and polymers synthesized in accordance with a preferred aspect of the present invention are typically represented by the formula:

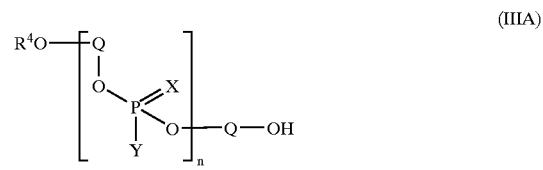

(IIIA)

wherein: Q, X, and n are as defined herein, and Y is any suitable heteroatom or organic substituent, preferably hydroxyl (or a suitable salt thereof). Preferably n is in the range from about 3 to about 200; more preferably, n is in the range from about 10 to about 40; and most preferably in the range from about 15 to about 25. In the polymers synthesized using the methods and compounds of the present invention, Q, X, and Y, or any combination thereof, can be the same or different when n is 1, and can be the same or different in each of the units defined by n when n is greater than 1.

$R^4$ is preferably a hydrogen or a hydroxyl protecting group such as, for example, a 4,4'-dimethoxytriphenylmethyl (DMTr), 4-methoxytriphenylmethyl (MMTr), pixyl, acetyl, 9-fluorenylmethyloxycarbonyl (Fmoc), t-butyldimethylsilyl (TBDMS), and the like. Alternatively, $R^4$ is a reporter group such as, for example, an amine, a mercapto, a phosphate, a phosphorothioate, and the like. Reporter groups preferably contain an active moiety for further reaction with radioactive label such as, for example, $^{32}$P-phosphate, $^{125}$-iodinated Bolton-Hunter reagent, and the like, or a non-radioactive label such as, for example, fluorescein isothiocyanate (FITC), dansyl chloride, and the like, or any other biologically active group such as, for example, biotin, digoxigenin, and the like. Reporter groups can be introduced by means known to those skilled in the art including, for example, introduction of appropriate linkers, spacers, arms, or other reagents used for manipulating the distance between the reporter group and the polymer.

X in formula (IIIA) is preferably S, O, or Se or a substituted imino of the formula $=NR^{16}$, wherein $R^{16}$ is an alkyl, an aryl, or an alkenyl-substituted aryl substituent. Preferably, Y is an OH (or suitable salt thereof).

In a preferred embodiment, P-chiral polymers of the present invention are of formula (IIIA) above, wherein X and Y, or any combination thereof, can be the same or different in any of the units being defined by n. More preferably, P-chiral oligonucleotides prepared in accordance with the present invention are of the formula:

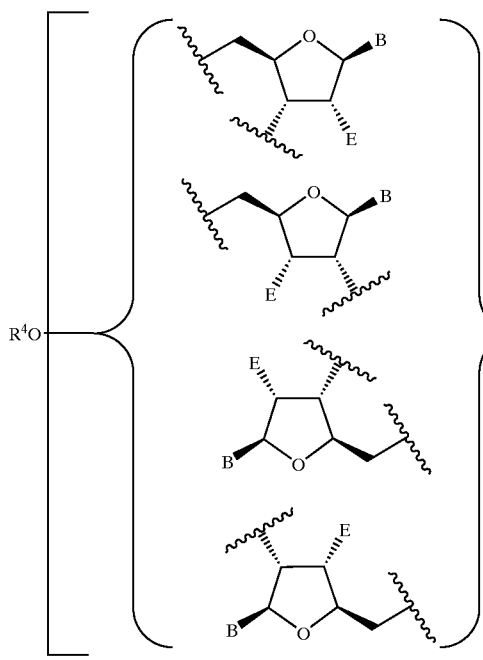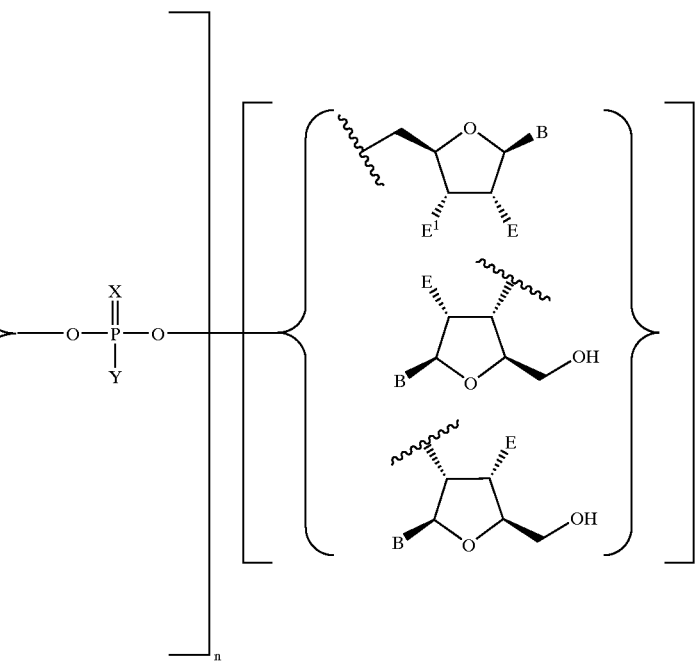

wherein X, Y, B, E and $R^4$ are as defined herein, and $E^1$ includes the same groups defined herein with respect to E, and E and $E^1$ can be the same or different. B is preferably a natural or a synthetically modified nucleic base, or B is a synthetic analog or reporter group, preferably a reporter group comprising a carboxyl, an alkyl, or an alkylamine. $E^1$ is preferably a 3'-hydroxyl (optionally protected), and E is preferably a hydrogen, a halogen, a hydroxyl, or an appropriately protected hydroxyl, an amine, or an appropriately protected amine, or the like.

A polymer of any suitable length can be prepared in accordance with the method of the present invention.

Preferably, n is in the range from about 3 to about 200, but is more preferably in the range from about 12 to about 60. It is understood that the P-chiral oligonucleotides of the invention can include linkages, for example, 5'-3', 5'-2', 5'-5', 3'-3', 2'-2', and 3'-2' linkages, between nucleosides by the appropriate selection of Q and $Q^1$, as defined herein.

The compounds of the present invention represented by formulae (I) and (II) are typically prepared from a synthon of the formula:

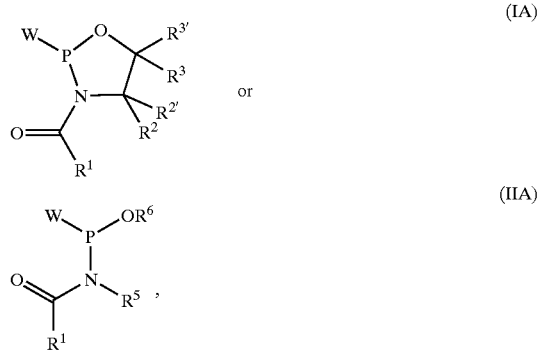

wherein $R^1$–$R^{3'}$, $R^5$, and $R^6$ are as defined herein, and W is a leaving group amenable to nucleophilic attack by a free group of the monomer, preferably a monomer of the formula $R^4$—O—Q—OH or $R^4$—O—$Q^1$—OH, wherein $R^4$, Q, and $Q^1$ are as defined herein. Preferably, W is halogen, a dialkylamino having from 2 to about 8 carbon atoms, or a cyclic amine substituent having from 2 to about 6 carbon atoms, wherein at least one carbon of the alkyl groups in the dialkylamino and cyclic amine substituents is optionally substituted with one or more heteroatoms, which are the same or different. More preferably W is Cl, dialkylamino, or a cyclic amino. Most preferably, W is diethylamino.

EXAMPLES

The following examples further illustrate the present invention but, of course, should not be construed as in any way limiting its scope.

Example 1

This example illustrates a general synthesis of the compounds of the present invention. The reaction schemes referenced in this example are generally illustrated in FIG. 1.

Typically, the synthon precursor 5 (FIG. 1) is synthesized by first refluxing a mixture of acrolein (1), trimethylsilyl cyanide, and catalytic amounts of zinc iodide according to the procedure reported by Gardrat et al. (*J. Heterocyclic Chem.* 1990, 27, 811). Reduction of the resulting nitrile 2 with $LiAlH_4$ in $Et_2O$ afforded amino-alcohol 3. Heating 3 with a slight excess (1.1 molar equiv) of ethyl fluoroacetate at 120° C. until all ethyl alcohol has distilled off gave the hydroxylated amide 4 in 88% yield (b.p. 83–84° C./0.1 torr). An equimolar solution of hexaethylphosphorus triamide and 4 was heated to 120° C. until all diethylamine has distilled off. Vacuum distillation afforded the oxazapholane 5 in 69% k yield.

Nucleoside cyclic acylphosphoramidite 7 was prepared by the reaction of a suitably protected nucleoside 6 with equimolar amounts of 5 and 1H-tetrazole in anhydrous dichloromethane for 4 h at ambient temperature. Following evaporation of the reaction mixture, the residue is purified using a short silica gel column chromatography. The nucleosidic synthon 7 is rapidly eluted with a solution of acetonitrile:chloroform (1:2 v/v). Removal of the eluent under reduced pressure afforded 7 as a white foam. The nucleoside cyclic acylphosphoramidite 9 is prepared in a similar manner from nucleoside 8 and compound 5.

Example 2

Figure 2:
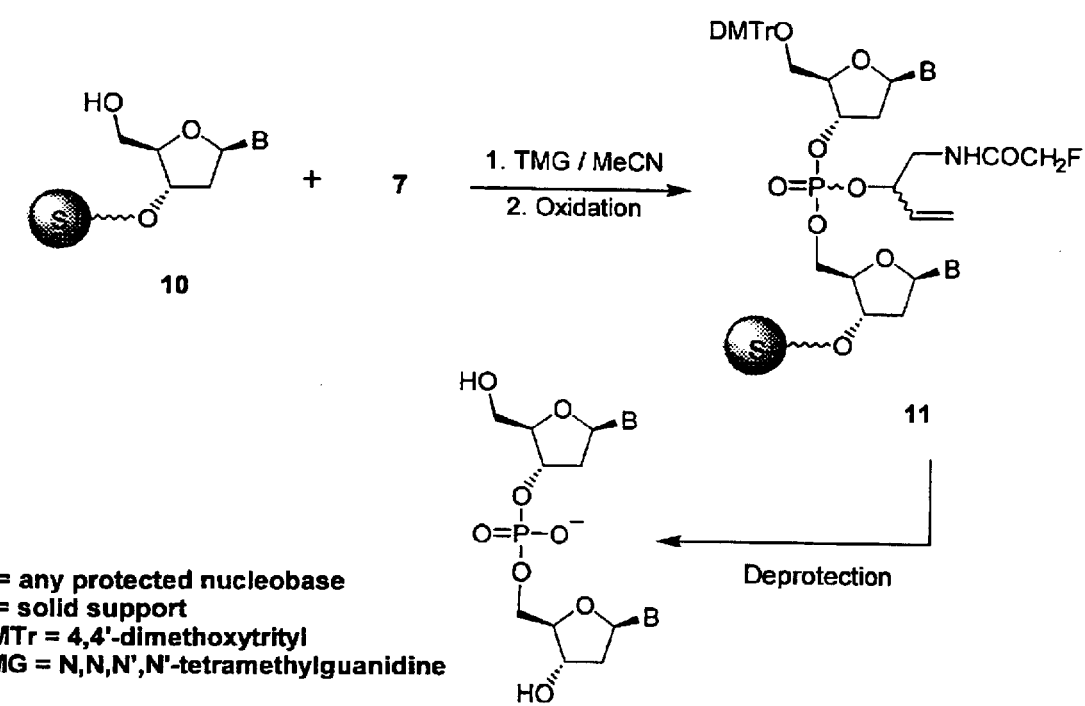
FIG. 2 illustrates a solid phase synthesis of an oligonucleotide.

This example illustrates a solid phase synthesis in accordance with the present invention. The general reaction scheme is illustrated in FIG. 2, in which nucleoside cyclic acylphosphoramidite 7 (FIG. 1) is specifically applied to the manual solid-phase synthesis of a decanucleotide ($dC_{10}$). A solid support is denoted in FIGS. 2 and 3 by a darkened sphere with "S" in the center.

Because of the sensitivity of standard succinyl linkers to strong bases, the first nucleoside monomer was attached to long chain alkylamine controlled pore glass (LCAA-CPG) to generate 10 has been modified. The attachment of the leader nucleoside to LCAA-CPG is accomplished via a sarcosine succinyl linkage according to the method of Brown et al. (*J. Chem. Soc. Chem. Commun.*, p. 891–893 (1989)). A column filled with 0.2 mmol of 10, wherein the 5'-OH was protected with a DMTr group, was treated with 2.5 mL of 3% trichloroacetic acid in dichloromethane for 1 min to ensure complete cleavage of the 5'-O-dimethoxytrityl (DMTr) protecting group. The column was then washed with 5 mL of acetonitrile (MeCN) and treated with a solution of 7 (10 mg) in 200 mL of 7.5% N,N,N',N'-tetramethylguanidine (TMG) in MeCN for 3 min. A solution (1 mL) of Cap A and Cap B (1:1) was pushed through the column, left for 1 min, and then washed with MeCN (5 mL), after which a solution of 1 M tert-butylhydroperoxide in dichloromethane (1 mL) was pushed through the column for 1 min, and washed with MeCN (5 mL). This cycle was repeated 8 additional times.

Stepwise DMTr analysis indicated that each coupling yield proceeded with high efficiency, typically 90% or greater. The content of the column was then transferred into a glass vial, and treated with concentrated ammonium hydroxide for 10 h at 55° C. The crude oligomer was characterized by reversed phase (RP) HPLC and polyacrylamide gel electrophoresis (PAGE). Both techniques indicated that $dC_{10}$ was prepared in a yield consistent with that determined by the stepwise DMTr analysis. In addition, crude $dC_{10}$ was cleanly hydrolysed by snake venom phosphodiesterase and alkaline phosphatase to 2'-deoxycytidine with no evidence of either partially deprotected nucleotides or nucleobase modifications. To enable, for example, the synthesis of thioated oligonucleotides stereogenically at phosphorus, the synthon 7 (FIG. 1) must first be separated into its Rp and Sp diastereoisomers (see FIG. 3). This is accomplished by chromatography on functionalized silica (C-1, C-2, C-4, C-8, or C-18 reversed-phase silica).

Example 3

This example illustrates the application of the synthetic "cycle" described in Example 2, in the stereospecific synthesis of oligonucleotide phosphorothioates. The reaction scheme is illustrated generally in FIG. 3.

Figure 3:
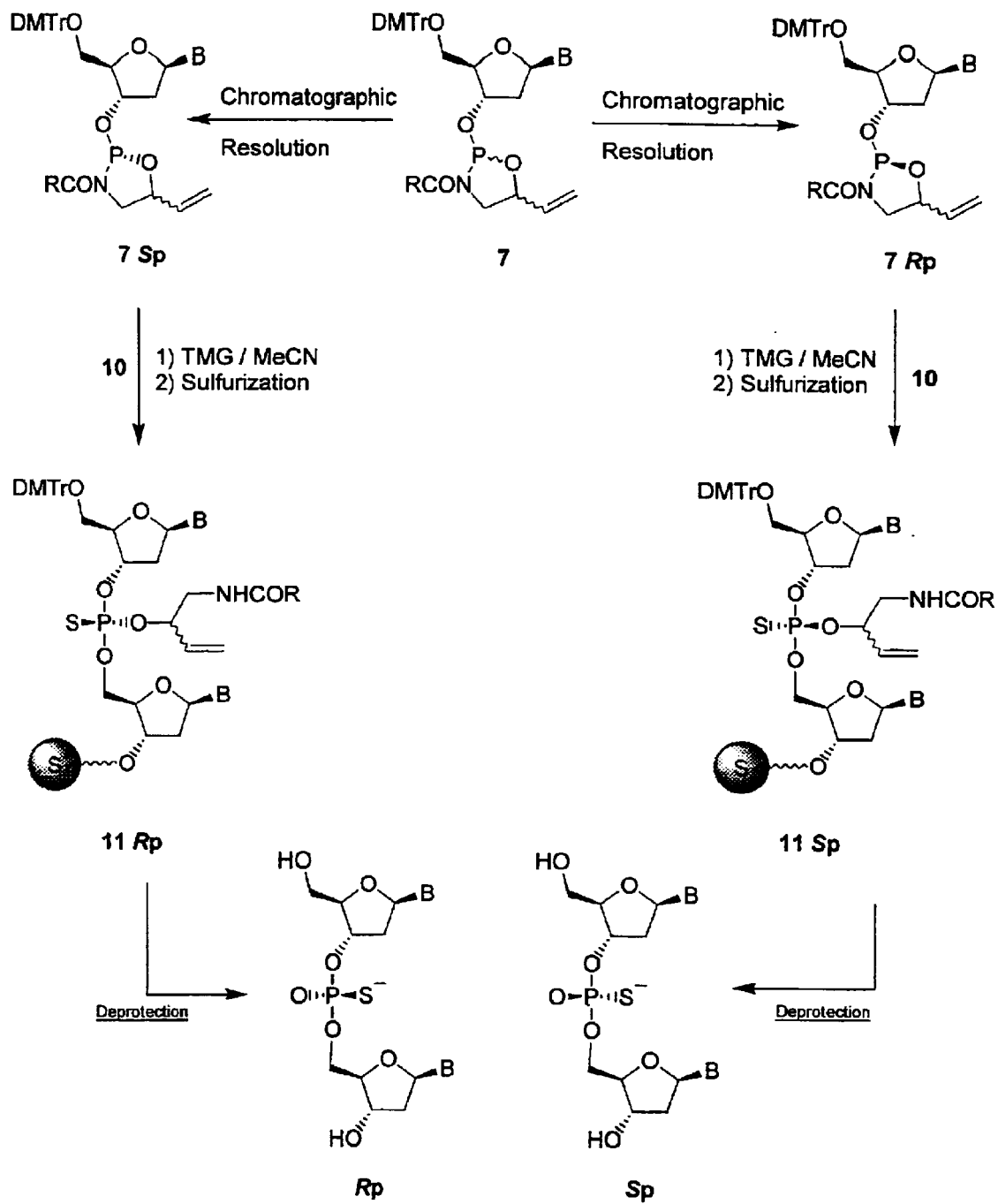
FIG. 3 illustrates the solid phase stereocontrolled synthesis of phosphorothioate oligonucleotides.

A diastereomeric mixture of nucleosidic N-acylphosphoramidite 7 was chromatographically separated into its Rp and Sp isomers 7Rp and 7Sp, respectively. Each P-chiral isomer was coupled with nucleophilic monomer 10 (FIG. 2), using the conditions of Example 2, to provide P-chiral adducts. The coupling reactions are stereospecific. Sulfurization of the resulting adducts results in the formation of the 11Sp and 11Rp isomers, as illustrated in FIG. 3. Deprotection of the solid support and the 2-amidoethoxy fragment from the sulfurized products is therefore expected to provide stereochemically pure Rp and Sp oligonucleotide products.

It should be noted that the oxidant in the oxidation step is replaced by a sulfur-transfer reagent such as 3H-1,2-benzodithiol-3-one 1,1-dioxide, phenylacetyl disulfide, bis (O,O-diisopropoxyphosphinothioyl) disulfide, and the like. In order to ensure optimum sulfurization, a capping step should be performed after the sulfur transfer step.

Example 4

This example illustrates the preparation of various nucleosidic N-acylphosphoramidites of the present invention, wherein the N-acyloxazaphospholane moiety is introduced at different hydroxyls of a differentially protected nucleoside core. The reaction schemes are illustrated generally in FIG. 4.

Using the procedure of Example 1, nucleophilic monomers 12, 14, 16, and 18 were coupled to synthon 5 using tetrazole, to provide nucleosidic N-acylphosphoramidites 13, 15, 17, and 19, respectively. The resulting nucleosidic N-acylphosphoramidites can be used as a vehicle for one or more coupling reactions, to provide oligomer or polymer products. Alternatively, the resulting nucleosidic N-acylphosphoramidites can be separated into their Rp and Sp isomers prior to their use as coupling reagents. The phospholane moiety of nucleosidic N-acylphosphoramidites 13, 15, 17, and 19 are attached to either the 3'- or 5'-hydroxyl in the case of 2'-deoxyribonucleosides or, additionally, to the 2'-hydroxyl in the case of ribonucleosides. These products also represent various ribonucleoside monomers that can be used for solid-phase synthesis (both stereospecific and non-stereospecific) of oligoribonucleotides and their analogues as illustrated in FIG. 2 and FIG. 3.

Example 5

This example illustrates the preparation of acyclic N-acylphosphoramidites, and methods of using them in the context of the present invention. The nucleoside acylphosphoramidites can be applied in a manner similar to that described in Examples 2 and 3, and FIG. 2 and FIG. 3. The reaction scheme is illustrated generally in FIG. 5. A solid support is denoted in FIG. 5 by a darkened sphere with "S" in the center.

Figure 5:
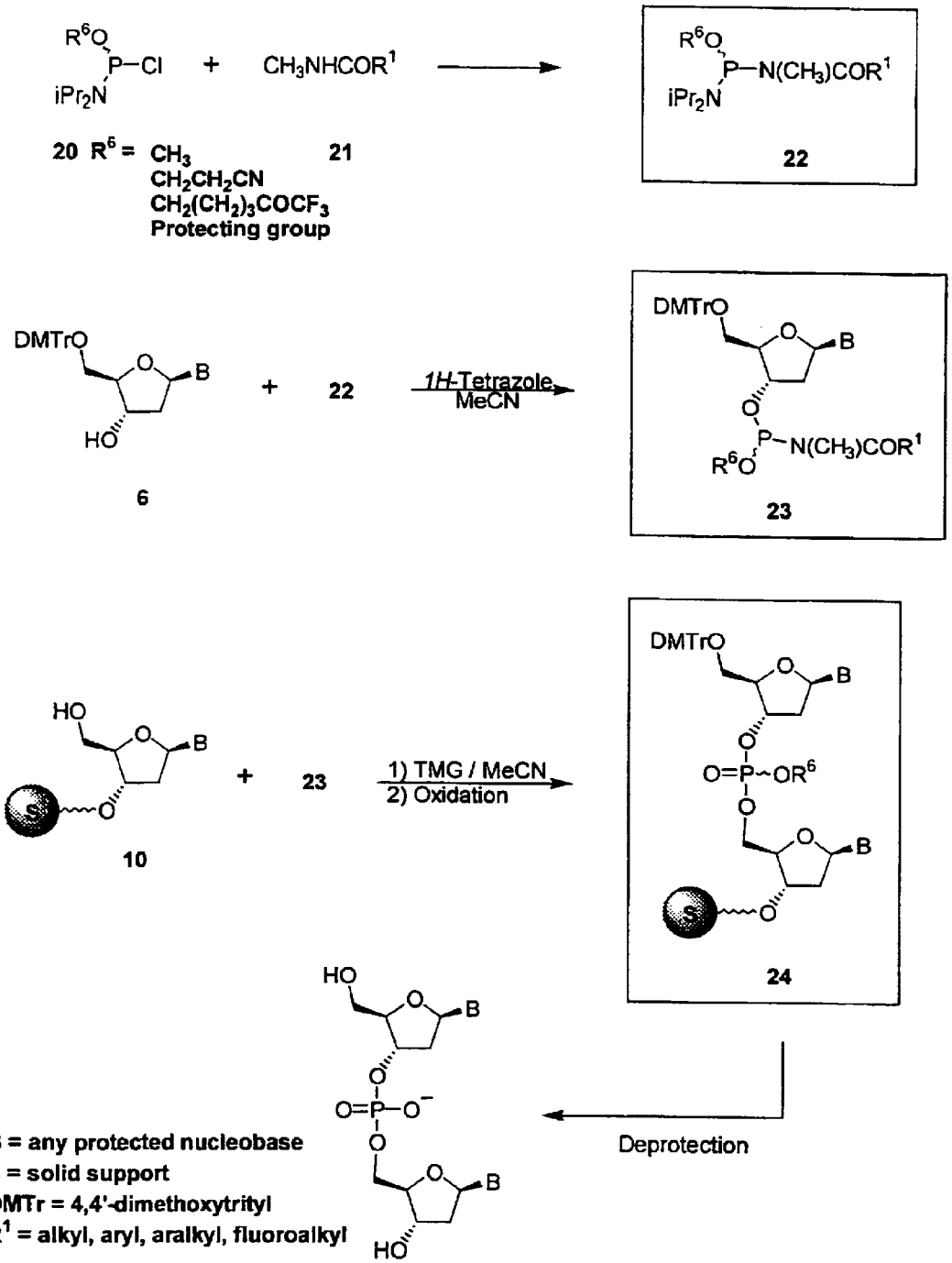
FIG. 5 illustrates the preparation of acyclic N-acylphosphoramidites and their application in solid phase syntheses.

As illustrated in FIG. 5, the non-nucleosidic chlorophosphoramidite derivative 20 is condensed with a suitable N-methylamide (21) to generate the acylphosphoramidite 22. Reaction of 22 with suitably protected nucleosides 6 (FIG. 1) in the presence of 1H-tetrazole affords the corresponding nucleoside 3'-acylphosphoramidites 23 as a mixture of P-diastereoisomers. These amidites are activated under basic conditions and are expected to be useful in solid-phase oligonucleotide synthesis in a manner similar to that shown in FIG. 2. Nucleoside 5'-acylphosphoramidites similar to 9 (FIG. 1) also can be applied for the same purpose. Alternatively, separation of the Rp- and Sp-diastereoisomers of 23 are expected to enable the stereospecic synthesis of thioated oligonucleotides in a manner similar to that illustrated in FIG. 3. In this context, ribonucleoside acylphosphoramidites of formula

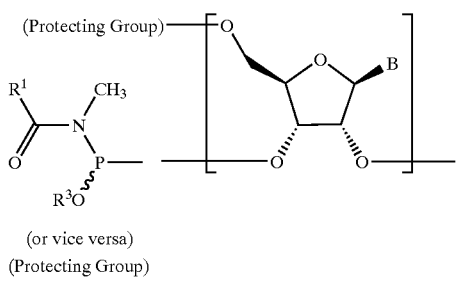

or

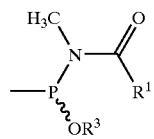

Figure 4:
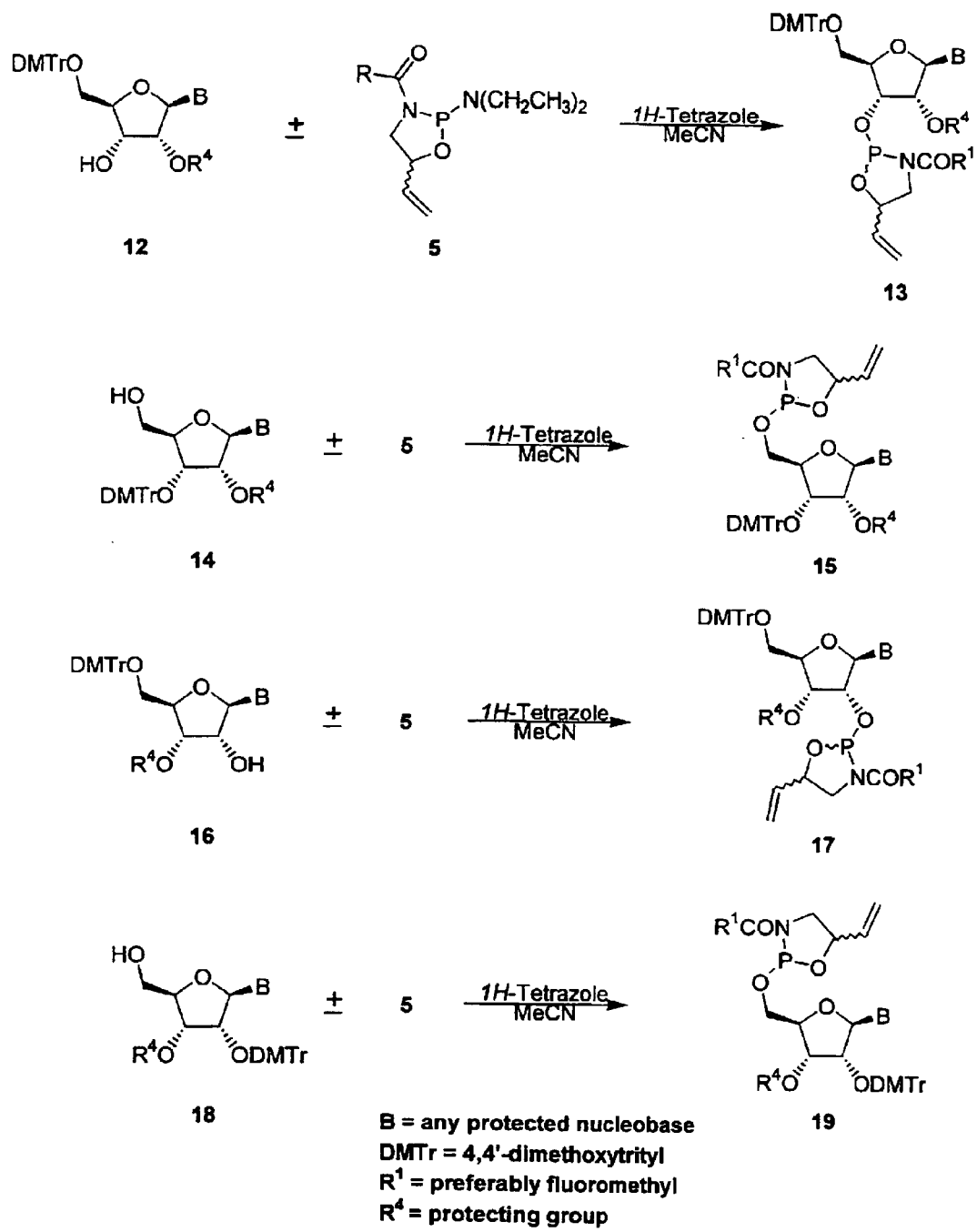
FIG. 4 illustrates the synthesis of various compounds of formula (I).

(or vice versa)
(Protecting Group)

can be used in accordance with the present invention for ribonucleotide syntheses, and are expected to work in the same manner as the cyclic species, for example, 13, 15, 17, and 19 (FIG. 4).

Example 6

Figure 6:
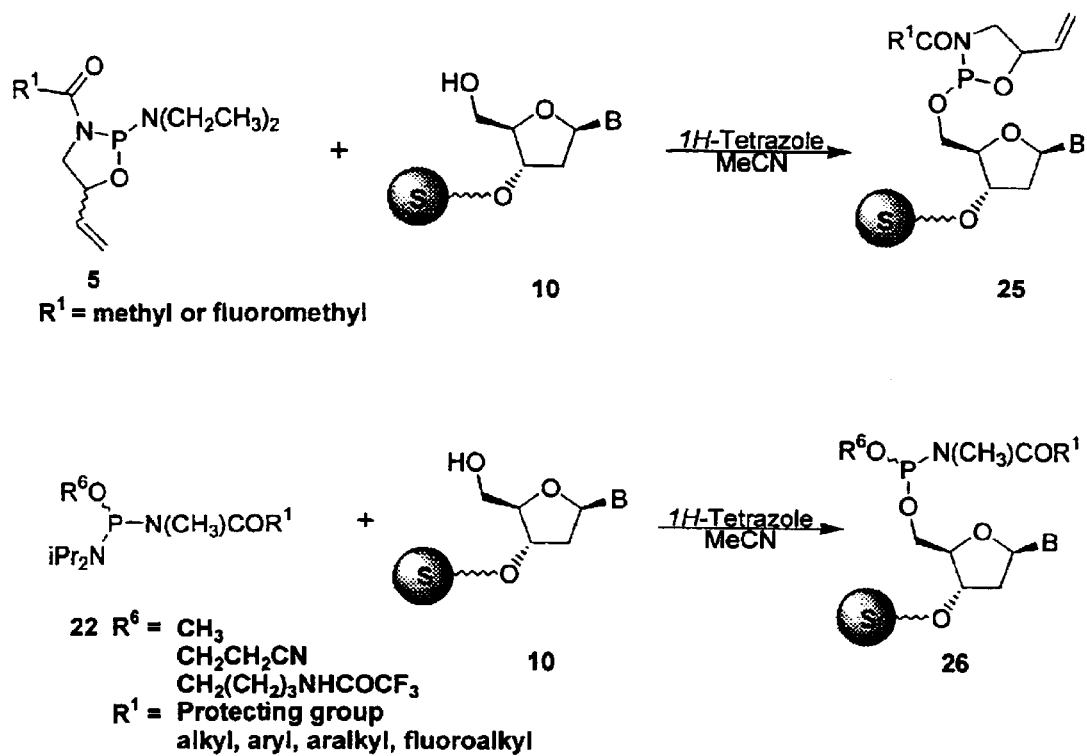
FIG. 6 illustrates an oligonucleotide synthesis using an alternative method.
Figure 7:
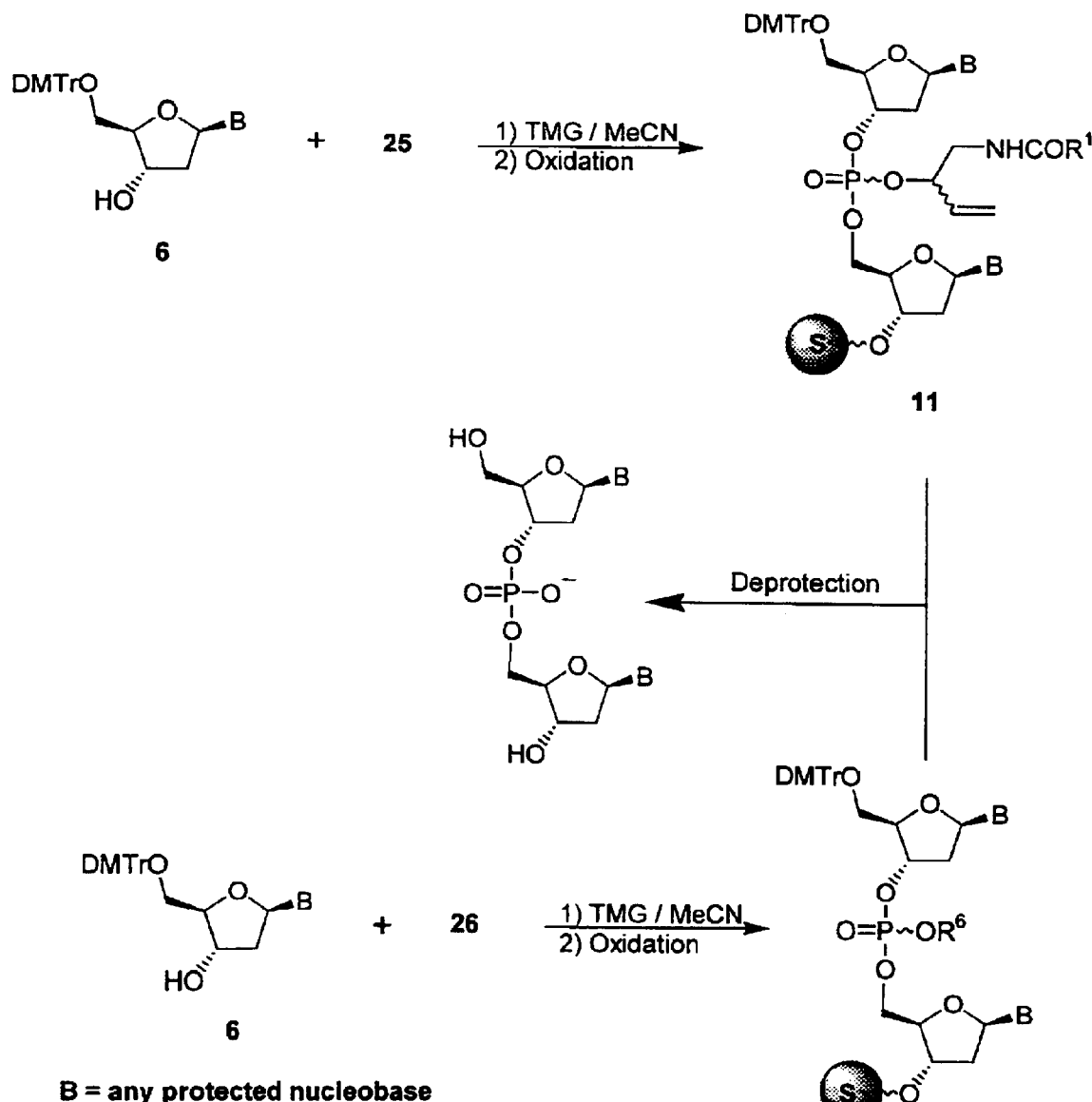
FIG. 7 illustrates the preparation of a particular oligonucleotide using either cyclic or acyclic N-acylphosphoramidites.

This example demonstrates an alternate approach to the synthesis of oligonucleotides via nucleoside cyclic acylphosphoramidites and acylphosphoramidites, as illustrated in FIGS. 6 and 7. A solid support is denoted in FIGS. 6 and 7 by a darkened sphere with "S" in the center. The strategy was demonstrated by reacting non-nucleosidic cyclic N-acylphosphoramidite 5 (FIG. 1) and acylphosphoramidite 22 (FIG. 5) with the functionalized solid-support-bound 10 (FIG. 2) in the presence of 1H-tetrazole to generate 25 and 26, respectively, as shown in FIG. 6. The reaction of suitably protected nucleoside 6 with 25, or 6 with 26, under basic conditions, followed by oxidation, provided dinucleotides 11 and 27, respectively (Scheme 7). Deprotection of 11 and 27 provides the same dinucleotide, as shown in FIG. 7. The same strategy applies with respect to the synthesis of ribonucleotide and the non-stereospecific synthesis of thioated oligonucleotides. The solid-phase synthesis of a decanucleotide ($dC_{10}$) has been achieved using a DNA synthesizer.

General Protocol for Examples 7–12

For the synthesis of oligonucleotides using 5'-O-dimethoxytrityl-3'-O-(5-phenyl-3-N-fluoroacetyl)-1,3,2-oxazaphospholanyl-2'-O-deoxyribonucleoside derivatives in examples 7–12, the general protocol is as follows. The syntheses were performed in a standard DNA synthesis column as available from many suppliers. Standard LCAA-CPG from Applied Biosystems (Masterpiece) columns were used.

The syntheses were carried out by way of the following general steps. The steps were not necessarily done in numerical order within a particular synthesis cycle. The particular sequence of steps used is indicated separately in each example.

In step 1, the appropriate CPG-bound nucleoside is detritylated in accordance with a standard procedure.

In step 2, 5'-O-Dimethoxytrityl-3'-O-(5-phenyl-3-N-fluoroacetyl)-1,3,2-oxazaphospholanyl-2l-O-deoxyribonucleoside derivatives (5 mg, ca. 5 μmol) are dissolved in acetonitrile (200 μL). Tetramethylguanidine (TMG, 4 μl, ca. 30 μmol) is subsequently added and the mixture is applied to the synthesis column.

In step 3, a standard oxidation or sulfurization reaction is carried out after the reaction of step 2 is continued for 5 min.

Steps 2 and 3 are repeated to optimize the yield for a particular synthesis cycle. Steps 2 and 3 need not be performed more than once for a particular synthesis cycle. However, yields are typically improved (e.g., resulting in nearly 100% overall yield) if steps 2 and 3 are repeated within a particular synthesis cycle. Optionally, steps 2 and 3 can be repeated three or more times, as desired, to optimize the yield for a particular synthesis cycle even further.

In step 4, the synthesis cycle is concluded with a capping step. Synthesis cycles can be repeated until the designed sequence length is obtained.

In step 5, the synthetic oligonucleotide is subjected to post-synthesis cleavage from the support, and deprotection.

Example 7

This example describes the synthesis of a dinucleotide, particularly TAT. The following steps were used in the present example.

Step 1: The bound nucleoside was treated with 3% trichloroacetic acid/dichloromethane (Applied Biosystems DNA synthesis reagent (3 mL, 1 min)), followed by washing with acetonitrile (3 mL, 30 s).

Step 2: 5'-O-Dimethoxytrityl-3'-O-(5-phenyl-3-N-fluoroacetyl)-1,3,2-oxazaphospholanyl-2'-O-deoxythymidine (5 mg, ca. 5 μmol) and tetramethylguanidine (TMG, 4 μl, ca. 30 μmol) in acetonitrile (200 μl) were added to the column and reacted for 5 min., followed by washing with acetonitrile (3 mL, 30 s).

Step 3: The resulting product was treated with iodine/water/pyridine/tetrahydrofuran (Applied Biosystems DNA synthesis reagent), (500 μl, 30 s), followed by washing with acetonitrile (3 ml, 30 s).

Step 5: The dinucleotide was cleaved from the support by treatment with concentrated aqueous ammonium hydroxide solution (1 mL, 10 h, 55° C.).

In the present example, a standard column DMT-T-LCAA-CPG (0.2 mmol) was used and was subjected to the above steps in the following sequence:

1, 2, 3, 2, 3, 1, 5

The ammoniacal solution obtained in the final step was concentrated under reduced pressure and analyzed by RP-HPLC.

Example 8

This example describes the synthesis of P-diasteriomerically pure phosphorothioate $[R_p]$-$C_{PS}C$. The following steps were used in the present example.

Step 1: The bound nucleoside was treated with 3% trichloroacetic acid/dichloromethane (Applied Biosystems DNA synthesis reagent), (3 mL, 1 min), followed by washing with acetonitrile (3 mL, 30 s).

Step 2: $[S_p]$-R-Benzoyl-5'-O-dimethoxytrityl-3'-O-(5-phenyl-3-N-fluoroacetyl)-1,3,2-oxazaphospholanyl-2'-O-deoxycytidine (5 mg, ca. 5 mmol) and tetramethylguanidine (TMG, 4 μl, ca 30 μmol) in acetonitrile (200 μl) were added to the column and reacted for 5 min., followed by washing with acetonitrile (3 mL, 30 s).

Step 3: The resulting product was treated with 3H-1,2-benzodithiol-3-one 1,1-dioxide (1% Beaucage Reagent in acetonitirile (w/v)), 3 min., followed by washing with acetonitirile (3 mL, 30 s).

Step 5: The dinucleotide was cleaved from the support by treatment with concentrated aqueous ammonium hydroxide solution (1 mL, 10 h, 55° C.)

In the present example, a standard column DMT-C$^{Bz}$-LCAA-CPG (0.2 μmol) was used and was subjected to the above steps in the following sequence:

1, 2, 3, 2, 3, 1, 5

The ammoniacal solution obtained in the final step was concentrated under reduced pressure and analyzed by RP-HPLC.

Example 9

This example describes the synthesis of a P-diastereomerically pure phosphorothioate-linked trinucleotide (trimer), [R$_p$,R$_p$]C$_{PS}$C$_{PS}$C. The following steps were used in the present example.

Step 1: The bound nucleoside was treated with 3% trichloroacetic acid/dichloromethane (Applied Biosystems DNA synthesis reagent), (3 mL, 1 min), followed by washing with acetonitirile (3 mL, 30 s).

Step 2: [Sp]-N-Benzoyl-5'-O-dimethoxytrityl-3'-O-(5-phenyl-N-fluoroacetyl)-1,3,2-oxazaphospholanyl-2'-O-deoxycytidine (FIG. 8B, 5 mg, ca. 5 mmol) and tetramethylguanidine (TMG, 4 μl, oxazaphospholanyl-2'-O-(5-phenyl-3-N-fluoroacetyl)-1,3,2-oxazaphospholanyl-2'-O-deoxycytidine (5 mg, ca. 5 μmol) and tetramethylguanidine (TMG, 4 μl, ca. 30 μmol) in acetonitrile (200 μl) were added to the column and reacted for 5 min., followed by washing with acetonitrile (3 mL, 30 s).

Step 3: The resulting product from step 2 was treated with 3H-1,2,-benzodithiol-3-one 1,1-dioxide (1% Beaucage Reagent in acetonitrile (w/v)), 3 min., followed by washing with acetonitrile (3 mL, 30 s).

Step 4: The resulting product from step 3 was capped with acetic anhydride/lutidine/tetrahydrofuran (Applied Biosystems DNA synthesis reagent), (1 mL), mixed with 1-methylimidazole/tetrahydrofuran (Applied Biosystems DNA synthesis reagent), (1 mL), 2 min., followed by washing with acetonitrile (3 mL, 30 s).

Step 5: The trinucleotide was cleaved from the support by treatment with concentrated aqueous ammonium hydroxide solution (1 mL, 10 h, 55° C.).

In the present example, a standard column DMT-C$^{Bz}$-LCAA-CPG (0.2 μmol) was used and was subjected to the above steps in the following sequence:

1, 2, 3, 2, 3, 4, 1, 2, 3, 2, 3, 5

Figure 8A:
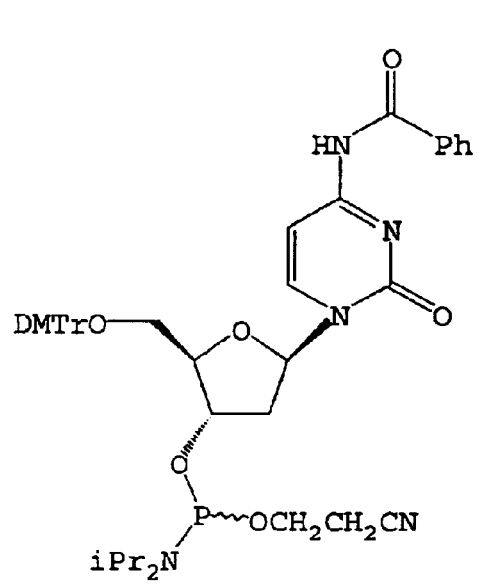
FIG. 8A illustrates the structure of a standard phosphoramidite coupling reagent used in conventional nucleotide coupling reactions.
Figure 8B:
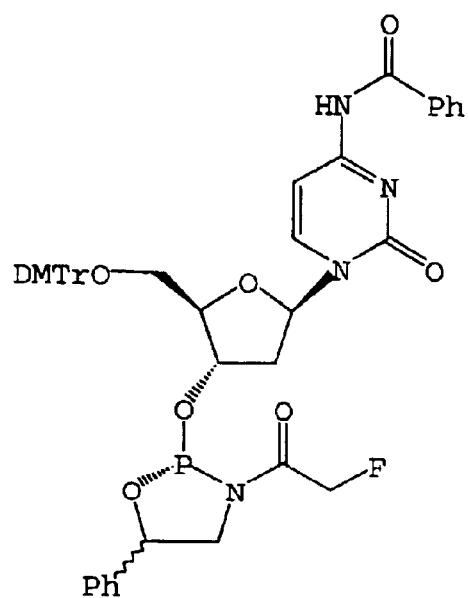
FIG. 8B illustrates the structure of a P-chiral ($S_p$) N-acylphosphoramidite of the present invention.

The ammoniacal solution obtained in the final step was concentrated under reduced pressure to provide the P-diastereomerically pure phosphorothioate-linked trinucleotide (trimer), [R$_p$,R$_p$]C$_{PS}$C$_{PS}$C. The product obtained in accordance with the present invention was analyzed by RP-HPLC (FIG. 10D). The trimer C$_{PS}$C$_{PS}$C also was prepared using a standard phosphoramidite coupling reagent (FIG. 8A). The HPLC of C$_{PS}$C$_{PS}$C obtained using the standard phosphoramidite coupling reagent is shown in FIG. 10A and contained, as expected, a mixture of all four possible P-diastereomers (indicated by RR, SR, RS, and SS). By contrast, the trimer prepared in accordance with the present invention produced only one P-diastereomer (RR). No other P-diastereomers were present by HPLC in the product obtained in accordance with the present invention, even in trace amounts. Co-injection of the trimer prepared in accordance with the present invention and the P-diastereomeric mixture obtained by the standard phosphoramidite method (FIG. 10E) confirmed that the product obtained in accordance with the present invention was indeed [R$_p$,R$_p$]C$_{PS}$C$_{PS}$C. This example demonstrates that the N-acylphosphoramidites of the present invention produce oligomers that are P-diastereomerically pure.

Example 10

This example describes the synthesis of a P-diastereomerically pure phosphorothioate-linked trinucleotide (trimer), [S$_p$,S$_p$]C$_{PS}$C$_{PS}$C. The following steps were used in the present example.

Step 1: The bound nucleoside was treated with 3% trichloroacetic acid/dichloromethane (Applied Biosystems DNA synthesis reagent), (3 mL, 1 min.), followed by washing with acetonitrile (3 mL, 30 s).

Figure 8C:
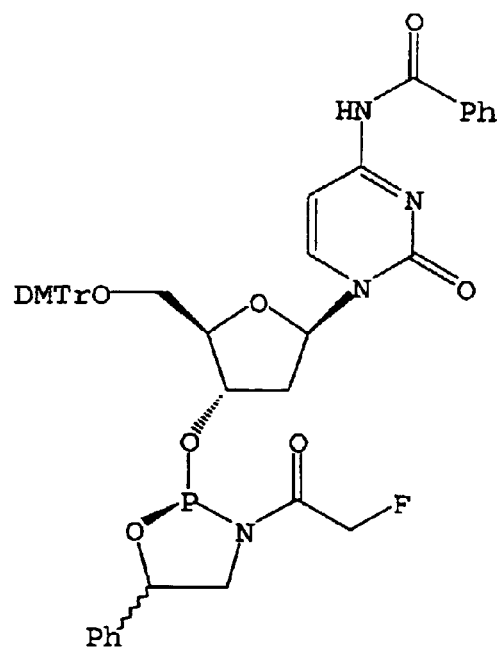
FIG. 8C illustrates the structure of a P-chiral ($R_p$) N-acylphosphoramidite of the present invention.

Step 2: [Rp]-N$^4$-Benzoyl-5'-O-dimethoxytrityl-3'-O-(5-phenyl-3-N-fluoroacetyl)-1,3,2-oxazaphospholanyl-2'-O-deoxycytidine (FIG. 8C, 5 mg, ca. 5 μmol) and tetramethylguanidine (TMG, 4 μl, ca. 30 μmol) in acetonitrile (200 μl) were added to the column and reacted for 5 min., followed by washing with acetonitrile (3 mL, 30 s).

Step 3: The resulting product from step 2 was treated with 3H-1,2-benzodithiol-3-one 1,1-dioxide (1% Beaucage Reagent in acetonitrile (w/v)), 3 min., followed by washing with acetonitrile (3 mL, 30 s).

Step 4: The resulting product from step 3 was capped with acetic anhydride/lutidine/tetrahydrofuran (Applied Biosystems DNA synthesis reagent), (1 mL), 2 min., followed by washing with acetonitrile (3 mL, 30 s).

Step 5: The trinucleotide was cleaved from the support by treatment with concentrated aqueous ammonium hydroxide solution (1 mL, 10 h, 55° C.).

In the present example, a standard column DMT-C$^{Bz}$-LCAA-CPG (0.2 μmol) was used and was subjected to the above steps in the following sequence:

1, 2, 3, 2, 3, 4, 1, 2, 3, 2, 3, 5

The ammoniacal solution obtained in the final step was concentrated under reduced pressure and analyzed by RP-HPLC. The product obtained in the present example was analyzed by RP-HPLC (FIG. 10B). The trimer C$_{PS}$C$_{PS}$C also was prepared using a standard phosphoramidite coupling reagent (FIG. 8A). The HPLC of the C$_{PS}$C$_{PS}$C obtained using the standard phosphoramidite coupling reagent is shown in FIG. 10A and contained, as expected, a mixture of all four possible P-diastereomers (indicated by RR, SR, RS, and SS). By contrast, the trimer prepared in accordance with the present invention produced only one P-diastereomer (SS). No other P-diastereomers were present by HPLC in the product obtained in accordance with the present invention, even in trace amounts. Co-injection of the trimer prepared in accordance with the present invention and the P-diastereomeric mixture obtained by the standard phosphoramidite method (FIG. 10C) confirmed that the product obtained in accordance with the present invention was indeed [S$_p$,S$_p$]C$_{PS}$C$_{PS}$C. This example further demonstrates that the N-acylphosphoramidites of the present invention produce oligomers that are P-diastereomerically pure.

Example 11

This example describes the synthesis of a P-diastereomerically pure phosphorothioate-linked tetramer [Rp,Sp,Rp]-C$_{PS}$C$_{PS}$C$_{PS}$C. The following steps were used in the present example.

Step 1: The bound nucleoside was treated with 3% trichloroacetic acid/dichloromethane (Applied Biosystems DNA synthesis reagent), (3 mL, 1 min.), followed by washing with acetonitrile (3 mL, 30 s).

Step 2: [S$_p$]-N$^4$-benzoyl-5'-O-dimethoxytrityl-3'-O-(5-phenyl-3-N-fluoroacetyl)-1,3,2,-oxazaphospholanyl-2'-O-deoxycytidine (5 mg, ca. 5 μmol) and tetramethylguanidine (TMG, 4 μl, ca. 30 μmol) in acetonitrile (200 μl) were added to the column and reacted for 5 min., followed by washing with acetonitrile (3 mL, 30 s).

Step 2': [Rp]-$N^4$-Benzoyl-5'-O-dimethoxytrityl-3'-O-(5-phenyl-3-N-fluoroacetyl)-1,3,2-oxazaphospholanyl-2'-O-deoxycytidine (FIG. 5C, 5 mg, ca. 5 μmol) and tetramethylguanidine (TMG, 4 μl, ca. 30 μmol) in acetonitrile (200 μl)) were added to the column and reacted for 5 min., followed by washing with acetonitrile (3 mL, 30 s).

Step 3: The resulting product from step 2 or 2' was treated with 3H-1,2-benzodithiol-3-one 1,1-dioxide (it Beaucage Reagent in acetonitrile (w/v)), 3 min., followed by washing with acetonitrile (3 mL, 30 s).

Step 4: The resulting product from step 3 was capped with acetic anhydride/lutidine/tetrahydrofuran (Applied Biosystems DNA synthesis reagent), (1 mL), mixed with 1-methylimidazole/tetrahydrofuran (Applied Biosystems DNA synthesis reagent), (1 mL), 2 min., followed by washing with acetonitrile (3 mL, 30 s).

Step 5: The trinucleotide was cleaved from the support by treatment with concentrated aqueous ammonium hydroxide solution (1 mL, 10 h, 55° C.).

In the present example, a standard column DMT-$C^{Bz}$-LCAA-CPG (0.2 μmol) was used and was subjected to the above steps in the following sequence:

1, 2, 3, 2, 3, 4, 1, 2', 3, 2', 3, 4, 1, 2, 3, 2, 3, 5

Figure 11A:
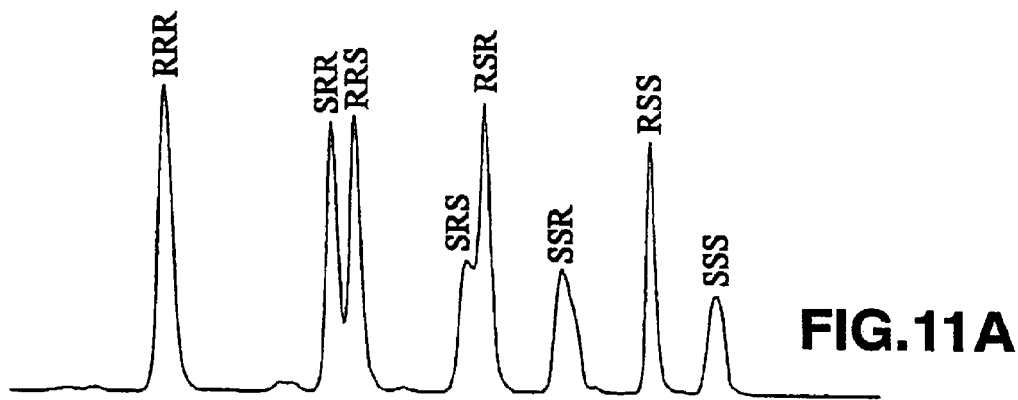
FIG. 11A illustrates the HPLC chromatogram for a mixture of the eight possible P-diastereomeric oligonucleotide phosphorothioate tetramers of $d(C_{PS}C_{PS}C_{PS}C)$ prepared using standard phosphoramidite chemistry.
Figure 11B:
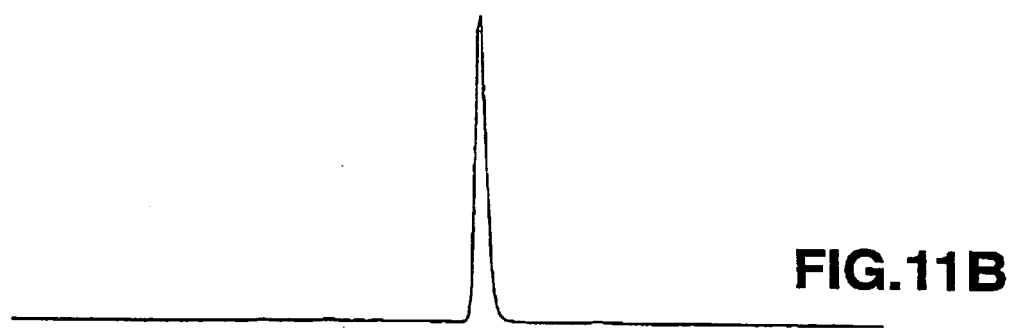
FIG. 11B illustrates the HPLC chromatogram for the pure $R_p,S_p,R_p$ diastereomer of $d(C_{PS}C_{PS}C_{PS}C)$ prepared in accordance with the present invention.

The ammoniacal solution obtained in the final step was concentrated under reduced pressure and analyzed by. RP-HPLC. The product obtained in the present example was analyzed by RP-HPLC (FIG. 11B).

Figure 11C:
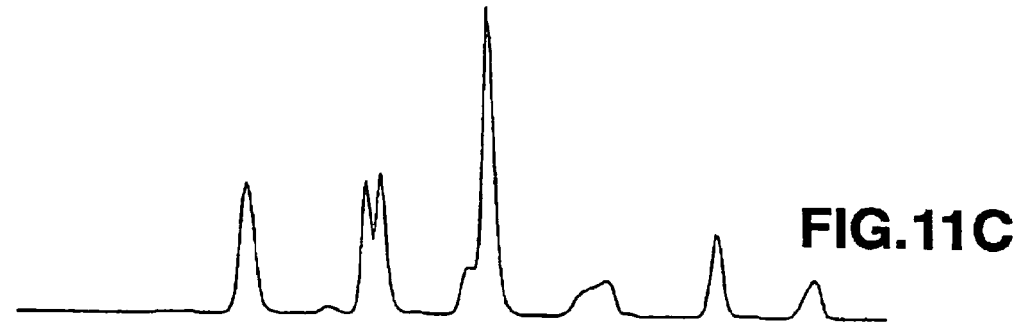
FIG. 11C illustrates the HPLC chromatogram obtained by co-injecting the pure $R_p,S_p,R_p$ diastereomer of d($C_{PS}C_{PS}C_{PS}C$) with the mixture containing all eight possible P-diastereomers.

The tetramer $C_{PS}C_{PS}C_{PS}C$ also was prepared using a standard phosphoramidite coupling reagent (FIG. 8A). The HPLC of the $C_{PS}C_{PS}C_{PS}C$ obtained using the standard phosphoramidite coupling reagent is shown in FIG. 11A and contained, as expected, a mixture of all eight possible P-diastereomers (indicated by RRR, SRR, RRS, SRS, RSR, SSR, RSS, and SSS). By contrast, the tetramer prepared in accordance with the present example produced only one P-diastereomer (RSR). No other P-diastereomers were present by HPLC, even in trace a amounts. Co-injection of the tetramer prepared in the accordance with the present invention and the P-diastereomeric mixture obtained by the standard phosphoramidite method (FIG. 11C) confirmed that the product obtained in accordance with the present invention was indeed [Rp,Sp,Rp]-$C_{PS}C_{PS}C_{PS}C$. This example further demonstrates that the N-acylphosphoramidites of the present invention can predictably produce oligomers that are P-diastereomerically pure.

Example 12

This example describes the synthesis of a P-diastereomerically pure phosphorothioate-linked undecamer, [all $R_p$]-[$T_{ps}$]$_{11}$T (eleven nucleoside units in the oligonucleotide chain). The following steps were used in the present example.

Step 1: The bound nucleoside was treated with 3 t trichloroacetic acid/dichloromethane (Applied Biosystems DNA synthesis reagent), (3 mL, 1 min.), followed by washing with acetonitrile (3 mL, 30 s).

Step 2: [Sp]-5'-O-Dimethoxytrityl-3'-O-(5-phenyl-3-N-fluoroacetyl)-1,3,2-oxazaphospholanyl-2'-O-deoxythymidine (5 mg, ca. 5 μmol) and tetramethylguanidine (TMG, 4 μl, ca. 30 μmol) in acetonitrile (200 μl) were added to the column and reacted for 5 min., followed by washing with acetonitrile (3 mL, 30 s).

Step 3: The resulting product from step 2 was treated with 3H-1,2-benzodithiol-3-one 1,1-dioxide (1% Beaucage Reagent in acetonitrile (w/v)), 3 min., followed by washing with acetonitrile (3 mL, 30 s).

Step 4: The resulting product from step 3 was capped with acetic anhydride/lutidine/tetrahydrofuran (Applied Biosystems DNA synthesis reagent), (1 mL), 2 min., followed by washing with acetonitrile (3 mL, 30 s).

Step 5: The trinucleotide was cleaved from the support by treatment with concentrated aqueous ammonium hydroxide solution (1 mL, 10 h, 55° C.).

In the present example, a standard column DMT-T-LCAA-CPG (0.2 μmol) was used and was subjected to the above steps in the following sequence:

[1, 2, 3, 2, 3, 4]$_{11}$, 5

The ammoniacal solution obtained in the final step was concentrated under reduced pressure and analyzed by RP-HPLC. The product obtained in the present example exhibited only one peak by HPLC. Although the HPLC system used in this example cannot chromatographically separate all possible P-diastereomers for an oligomer of this length, it is believed that the product obtained in the present example is indeed P-diastereomerically pure.

Example 13

Figure 9A:
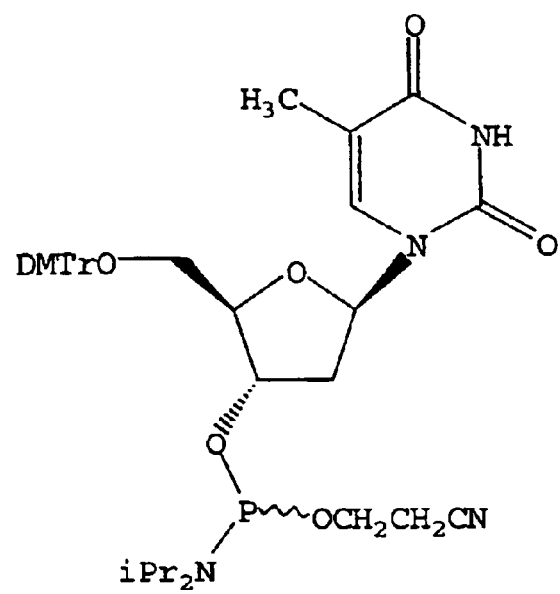
FIG. 9A illustrates the structure of a standard phosphoramidite coupling reagent used in conventional nucleotide coupling reactions.
Figure 9B:
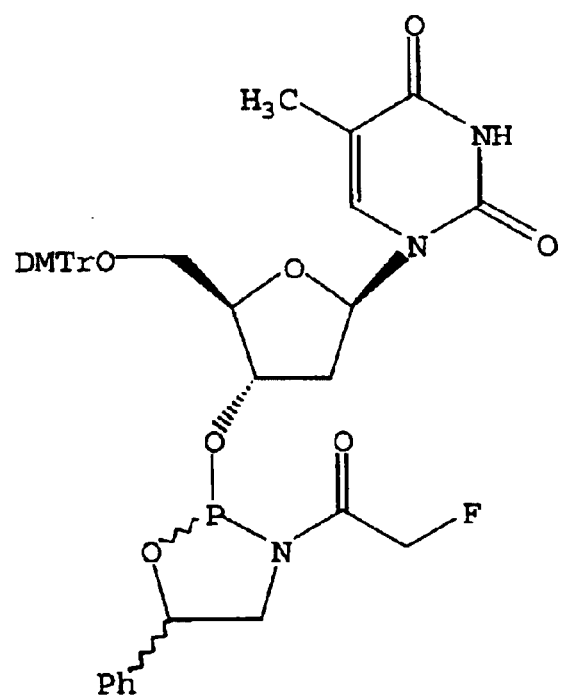
FIG. 9B illustrates the structure of a P-diastereomeric ($R_p,S_p$) N-acylphosphoramidite of the present invention.

This example demonstrates the hydrolytic stability of the N-acylphosphoramidites of the present invention (FIG. 9B), relative to the hydrolytic stability of standard phosphoramidites (FIG. 9A). The hydrolytic stability for each type of reagent was determined under reaction conditions normally employed for each type of coupling reagent.

Samples of the dinucleotide d($T_{PO}$G) were prepared by a standard coupling method using the phosphoramidite of FIG. 9A. Samples of d($T_{PO}$G) also were prepared by a coupling reaction in accordance with the present invention using the N-acylphosphoramidite of FIG. 9B. Each coupling method was performed in the absence of moisture and in the presence of moisture (0.1% water) The products were analyzed by HPLC. The HPLC chromatogram of the product obtained via the standard phosphoramidite reagent (FIG. 9A) in a moisture-free environment is shown in FIG. 12A. The HPLC chromatogram of the product obtained using the standard phosphoramidite of FIG. 9A in the presence of 0.1% moisture is shown in FIG. 12B. The HPLC chromatogram of the product obtained via the N-acylphosphoramidite (FIG. 9B) in a moisture-free environment is shown in FIG. 12C. The product obtained using the N-acylphosphoramidite of FIG. 9B in the presence of 0.1% moisture is shown in FIG. 12D.

The target product is indicated in the HPLC chromatogram by a peak labeled d($T_{PO}$G), corresponding to the dinucleotide. Hydrolysis of the coupling reagent (i.e., hydrolytic instability) is indicated in the HPLC chromatogram by the presence of a peak corresponding to the single nucleoside, indicated by dG.

The HPLC's confirmed that the same product (d($T_{PO}$G)) was obtained by either method when the reactions were carried out in a moisture-free environment (FIGS. 12A and 12C). However, when the same reactions were carried out in the presence of moisture, the product obtained by the standard phosphoramidite method contained only a trace of the desired product, and was almost entirely the uncoupled single nucleoside dG (FIG. 12B). Thus, as expected, the standard phosphoramidite was hydrolytically unstable under coupling conditions in which moisture was present. By contrast, the product obtained using the N-acylphosphoramidite (FIG. 9B) contained mostly the desired product, and a relatively minor amount of the uncoupled single nucleoside dG, even when the coupling reaction was performed in the presence of significant moisture (FIG. 12D). These results demonstrate that the N-acylphosphoramidites of the present invention are hydrolytically stable, even in the presence of a significant amount of moisture, under coupling conditions used in connection with such compounds.

All of the references cited herein, including patents, patent applications, and publications, are hereby incorporated in their entireties by reference.

While this invention has been described with an emphasis upon preferred embodiments, it will be obvious to those of ordinary skill in the art that variations of the preferred embodiments may be used and that it is intended that the invention may be practiced otherwise than as specifically described herein. Accordingly, this invention includes all modifications encompassed within the spirit and scope of the invention as defined by the following claims.

What is claimed is:

1. A compound of the formula:

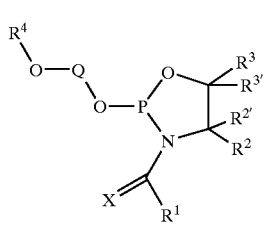
(I)

wherein:

R$^1$ is an alkyl, an alkenyl, an alkynyl, a cycloalkyl, an aryl, or an aralkyl, wherein R$^1$ is unsubstituted or substituted with one or more substituents, which are the same or different selected from the group consisting of R$^7$, OR$^7$, SR$^7$, NR$^8$COR$^7$, NR$^8$CSR$^7$, NR$^8$CO$_2$R$^7$, NR$^8$C(O)SR$^7$, NR$^8$CS$_2$R$^7$, O$_2$CR$^7$, S$_2$CR$^7$, SCOR$^7$, OCSR$^7$, SO$_2$R$^7$, OSO$_2$R$^7$, NR$^8$SO$_2$R$^7$, CN, NO$_2$, N$_3$, and a halogen, wherein R$^7$ is an alkyl, an aryl or an aralkyl, wherein R$^7$ is unsubstituted or substituted with one or more halogen atoms, which are the same or different, and R$^8$ is H or an alkyl;

R$^2$ and R$^{2'}$ are the same or different and each is H, an alkyl, an alkenyl, an alkynyl, a cycloalkyl, an aryl, or an aralkyl, wherein R$^2$ is unsubstituted or substituted with one or more substituents, which are the same or different, selected from the group consisting of OR$^7$, CN, NO$_2$, N$_3$, and a halogen;

R$^3$ and R$^{3'}$ are the same or different and each is H, an alkyl, an alkenyl, an alkynyl, a cycloalkyl, an aryl, or an aralkyl, wherein R$^3$ is unsubstituted or substituted with one or more substituents, which are the same or different, selected from the group consisting of a trialkylsilyl, an aryldialkylsilyl, an alkyldiarylsilyl, CN, NO$_2$, N$_3$, halogens, OR$^7$, P(O)(OR$^7$)(OR$^8$), COR$^9$, CSR$^9$, CO$_2$R$^9$, COSR$^9$, CSOR$^9$, CONR$^8$R$^9$, CSNR$^8$R$^9$, SO$_2$R$^9$, and SO$_2$NR$^8$R$^9$, wherein R$^9$ is H, an alkyl, an alkenyl, an alkynyl, a cycloalkyl, an aralkyl, or an aryl, wherein R$^9$ is unsubstituted or substituted with one or more substituents, which are the same or different, selected from the group consisting of CN, NO$_2$, N$_3$, and a halogen; or R$^2$ and R$^3$, R$^{2'}$ and R$^3$, R$^2$ and R$^{3'}$, or R$^{2'}$ and R$^{3'}$, together with the carbon atoms to which they are bonded, form a cyclic substituent of the formula:

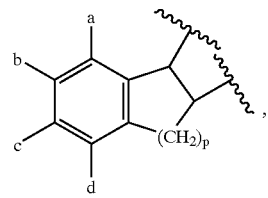

wherein p is an integer from 0–6 and a–d are the same or different and each is selected from the group consisting of H, an alkyl, a nitro, an amino, a hydroxy, a thio, a cyano and a halogen;

R$^4$ is a protecting group or a solid support;

Q is a nucleoside, an oligonucleotide having a nucleoside, or an oligomer having a nucleoside, wherein the nucleoside is of the formula:

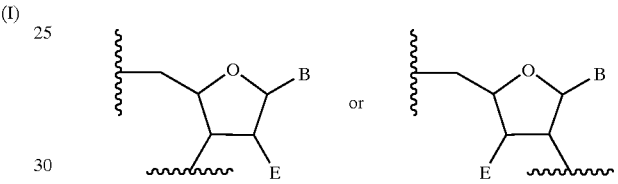

wherein:

B is a labeling group, an alkyl, an alkenyl, an alkynyl, a cycloalkyl, an aryl, a heteroaryl, a heterocycloalkyl, an aralkyl, an amino, an alkylamino, a dialkylamino, a purine, a pyrimidine, adenine, guanine, cytosine, uracil, or thymine, wherein B is unsubstituted or substituted with one or more substituents, which are the same or different, selected from the group consisting of a protecting group, R$^{11}$, OR$^{11}$, NHR$^{11}$, NR$^{11}$R$^{12}$, CN, NO$_2$, N$_3$, and a halogen, wherein R$^{11}$ and R$^{12}$ are the same or different and each is H, a protecting group, or an alkyl; and, E is H, a halogen, OR$^{13}$, NHR$^{13}$, or NR$^{13}$R$^{14}$, wherein R$^{13}$ and R$^{14}$ are the same or different and each is H, a protecting group, an alkyl, or an acyl; and X is O, S, or Se, wherein the labeling group is a carboxyl to which is appended, via an amide linker, biotin, cholesterol, fluorenylmethoxycarbonyl (Fmoc), or trifluoroacetyl.

2. The compound of claim 1, wherein Q is a nucleoside of the formula:

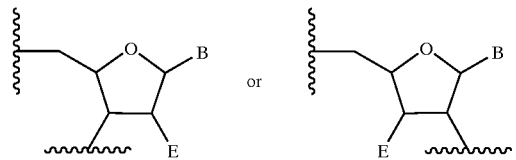

wherein B and E are as defined in claim 1.

3. The compound of claim 1, wherein the compound is of the formula:

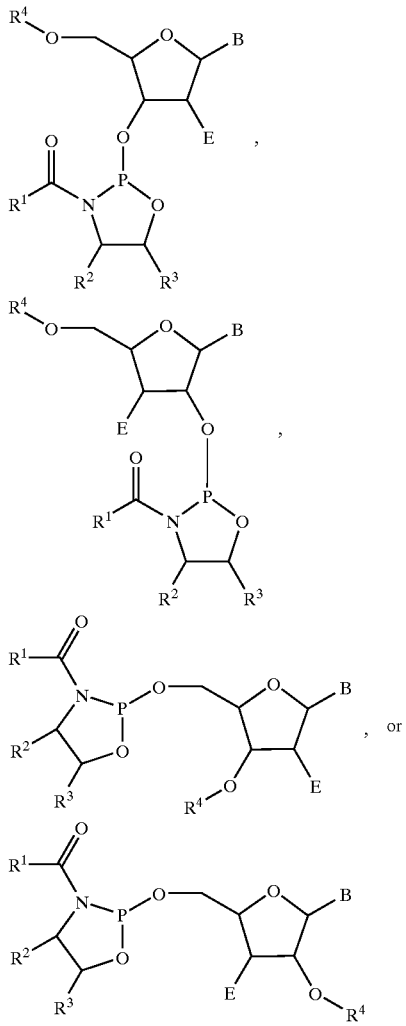

wherein $R^1$–$R^4$, B, and E are as defined in claim 1.

4. The compound of claim 1, wherein Q is an oligonucleotide having a nucleoside, a nucleoside, or an oligomer having a nucleoside, wherein the nucleoside is of the formula:

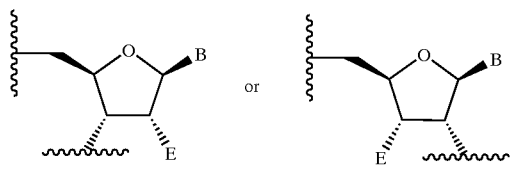

wherein B and E are as defined in claim 1.

5. The compound of claim 4, wherein B is a purine, a pyrimidine, adenine, guanine, cytosine, uracil, or thymine, wherein B is unsubstituted or substituted with one or more substituents, which are the same or different, selected from the group consisting of a protecting group, $R^{11}$, $OR^{11}$, $NHR^{11}$, $NR^{11}R^{12}$, CN, $NO_2$, $N_3$, and a halogen, wherein $R^{11}$ and $R^{12}$ are the same or different and each is H, a protecting group, or an alkyl.

6. The compound of claim 1, wherein $R^1$ is an alkyl, which is unsubstituted or substituted with one or more substituents, which are the same or different, selected from the group consisting of fluorine, $OR^7$, and $SR^7$, wherein $R^7$ is an alkyl or an aryl.

7. The compound of claim 6, wherein $R^3$ is a vinyl group or a phenyl group.

8. The compound of claim 1, wherein $R^4$ is a 4,4'-dimethoxytrityl group.

9. A method of preparing a polymer, the method comprising the steps of:
(a) reacting a nucleophile of the formula $R^4$—O—O—OH with the N-acylphosphoramidite of claim 1, wherein $R^4$ and O are as defined in claim 1, to produce an adduct of the N-acylphosphoramidite and the nucleophile, the adduct comprising a tricoordinated phosphorus atom;
(b) reacting the adduct with a reagent selected from the group consisting of oxidizing agents, sulfurizing agents, and selenizing agents, to produce a product, wherein the tricoordinated phosphorus atom is converted into a phosphorus atom with a valence of greater than three;
(c) removing the protecting group $R^4$ from the product; and
(d) optionally repeating steps (a) through (c) one or more times until a polymer of specified length is obtained.

10. The method of claim 9, further comprising the step of cleaving the bond linking the organic moiety to the non-bridging phosphate, phosphorothioate or phosphoroselenoate oxygen atom in the product obtained in step (c) or (d).

11. The method of claim 10, wherein the bond linking the organic moiety to the non-bridging phosphate, phosphorothioate or phosphoroselenoate oxygen atom is cleaved chemically.

12. The method of claim 10, wherein the bond linking the organic moiety to the non-bridging phosphate, phosphorothioate or phosphoroselenoate oxygen atom is cleaved thermally.

13. The method of claim 9, wherein the nucleophile is attached to a solid support.

14. The method of claim 9, wherein the nucleophile is of the formula:

$$R^4—O—Q—OH$$

wherein:
Q is a nucleoside, oligonucleotide having a nucleoside, or an oligomer having a nucleoside, wherein the nucleoside is of the formula:

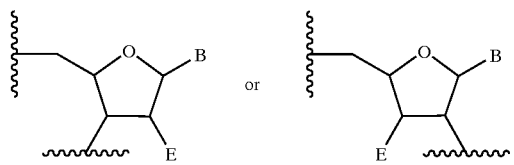

wherein:
B is a labeling group, an alkyl, an alkenyl, an alkynyl, a cycloalkyl, an aryl, a heteroaryl, a heterocycloalkyl, an aralkyl, an amino, an alkylamino, a dialkylamino, a purine, a pyrimidine, adenine, guanine, cytosine, uracil, or thymine, wherein B is unsubstituted or substituted with one or more substituents, which are the same or different, selected from the group consisting of a protecting group, $R^{11}$, $OR^{11}$, $NHR^{11}$, $NR^{11}R^{12}$, CN, $NO_2$, $N_3$, and a halogen, wherein $R^{11}$ and $R^{12}$ are the same or different and each is H, a protecting group, or an alkyl; and
E is H, a halogen, $OR^{13}$, $NHR^{13}$, or $NR^{13}R^{14}$, wherein $R^{13}$ and $R^{14}$ are the same or different and each is H, a protecting group, an alkyl, or an acyl; and
$R^4$ is a solid support.

15. The method of claim 14, wherein Q is a nucleoside, an oligonucleotide having a nucleoside, or an oligomer having a nucleoside, wherein the nucleoside is of the formula:

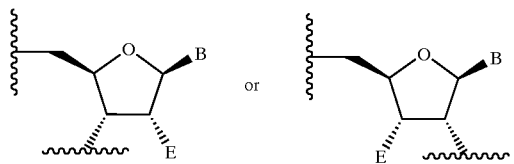

wherein B and E are as defined in claim 14.

16. The method of claim 9, wherein the N-acylphosphoramidite is of the formula:

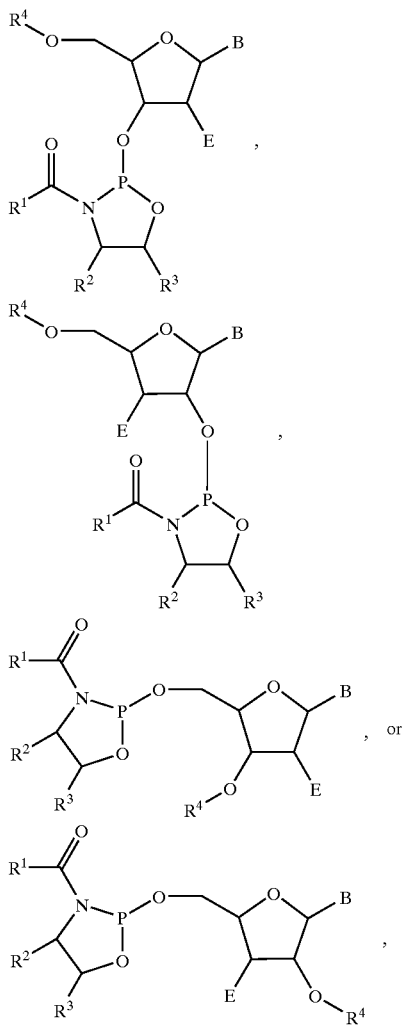

wherein:

$R^1$ is an alkyl, an alkenyl, an alkynyl, a cycloalkyl, an aryl, or an aralkyl, wherein $R^1$ is unsubstituted or substituted with one or more substituents, which are the same or different, selected from the group consisting of $R^7$, $OR^7$, $SR^7$, $NR^8COR^7$, $NR^8CSR^7$, $NR^8CO_2R^7$, $NR^8C(O)SR^7$, $NR^8CS_2R^7$, $O_2CR^7$, $S_2CR^7$, $SCOR^7$, $OCSR^7$, $SO_2R^7$, $OSO_2R^7$, $NR^8SO_2R^7$, CN, $NO_2$, $N_3$, and a halogen, wherein $R^7$ is an alkyl, an aryl or an aralkyl, wherein $R^7$ is unsubstituted or substituted with one or more halogen atoms, which are the same or different, and $R^8$ is H or an alkyl;

$R^2$ is H, an alkyl, an alkenyl, an alkynyl, a cycloalkyl, an aryl, or an aralkyl, wherein $R^2$ is unsubstituted or substituted with one or more substituents, which are the same or different, selected from the group consisting of $OR^7$, CN, $NO_2$, $N_3$, and a halogen;

$R^3$ is H, an alkyl, an alkenyl, an alkynyl, a cycloalkyl, an aryl, or an aralkyl, wherein $R^3$ is unsubstituted or substituted with one or more substituents, which are the same or different, selected from the group consisting of a trialkylsilyl, an aryldialkylsilyl, an alkyldiarylsilyl, CN, $NO_2$, $N_3$, a halogen, $OR^7$, $P(O)(OR^7)(OR^8)$, $COR^9$, $CSR^9$, $CO_2R^9$, $COSR^9$, $CSOR^9$, $CONR^8R^9$, $CSNR^8R^9$, $SO_2R^9$, and $SO_2NR^8R^9$, wherein $R^9$ is H, an alkyl, an alkenyl, an alkynyl, a cycloalkyl, or an aryl, wherein $R^9$ is unsubstituted or substituted with one or more substituents, which are the same or different, selected from the group consisting of CN, $NO_2$, $N_3$, and a halogen; or $R^2$ and $R^3$, together with the carbon atoms to which they are bonded, form a cyclic substituent of the formula:

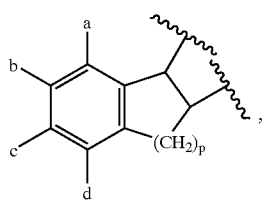

wherein p is an integer from 0–6 and a–d are the same or different and each is selected from the group consisting of H, an alkyl, a nitro, an amino, a hydroxy, a thio, a cyano and a halogen;

$R^4$ is a protecting group or a solid support;

B is a labeling group, an alkyl, an alkenyl, an alkynyl, a cycloalkyl, an aryl, a heteroaryl, a heterocycloalkyl, an aralkyl, an amino, an alkylamino, a dialkylamino, a purine, a pyrimidine, adenine, guanine, cytosine, uracil, or thymine, wherein B is unsubstituted or substituted with one or more substituents, which are the same or different, selected from the group consisting of a protecting group, $R^{11}$, $OR^{11}$, $NHR^{11}$, $NR^{11}R^{12}$, CN, $NO_2$, $N_3$, and a halogen, wherein $R^{11}$ and $R^{12}$ are the same or different and each is H, a protecting group, or an alkyl; and, E is H, a halogen, $OR^{13}$, $NHR^{13}$, or $NR^{13}R^{14}$, wherein $R^{13}$ and $R^{14}$ are the same or different and each is H, a protecting group, an alkyl, or an acyl.

17. The method of claim 16, wherein B is a purine, a pyrimidine, adenine, guanine, cytosine, uracil, or thymine, wherein B is unsubstituted or substituted with one or more substituents, which are the same or different, selected from the group consisting of a protecting group, $R^{11}$, $OR^{11}$, $NHR^{11}$, $NR^{11}R^{12}$, CN, $NO_2$, $N_3$, and a halogen, wherein $R^{11}$ and $R^{12}$ are the same or different and each is H, a protecting group, or an alkyl.

18. The method of claim 16, wherein $R^1$ is an alkyl, which is unsubstituted or substituted with one or more substituents, which are the same or different, selected from the group consisting of fluorine, $OR^7$, and $SR^7$, wherein $R^7$ is an alkyl, an aryl, or an aralkyl.

19. The method of claim 16, wherein $R^3$ is a vinyl group, a phenyl, or a benzyl.

20. The method of claim 16, wherein $R^4$ is a 4,4'-dimethoxytrityl.

* * * * *